US007920994B2

(12) United States Patent
Palsson et al.

(10) Patent No.: US 7,920,994 B2
(45) Date of Patent: *Apr. 5, 2011

(54) METHOD FOR THE EVOLUTIONARY DESIGN OF BIOCHEMICAL REACTION NETWORKS

(75) Inventors: Bernhard O. Palsson, La Jolla, CA (US); Jeremy S. Edwards, Newark, DE (US)

(73) Assignee: The Regents of the University of California, Oakland, CA (US)

( * ) Notice: Subject to any disclaimer, the term of this patent is extended or adjusted under 35 U.S.C. 154(b) by 188 days.

This patent is subject to a terminal disclaimer.

(21) Appl. No.: 11/584,368

(22) Filed: Oct. 19, 2006

(65) Prior Publication Data

US 2007/0055457 A1   Mar. 8, 2007

Related U.S. Application Data

(63) Continuation of application No. 09/940,686, filed on Aug. 27, 2001, now Pat. No. 7,127,379.

(60) Provisional application No. 60/265,554, filed on Jan. 31, 2001.

(51) Int. Cl.
*G06F 7/60* (2006.01)
*G06F 19/00* (2011.01)
*G06N 7/00* (2006.01)
*C12N 15/09* (2006.01)

(52) U.S. Cl. .............. 703/2; 703/11; 435/455; 435/468; 435/471; 702/19

(58) Field of Classification Search ........................ None
See application file for complete search history.

(56) References Cited

U.S. PATENT DOCUMENTS

| | | | |
|---|---|---|---|
| 5,273,038 A | 12/1993 | Beavin et al. | |
| 5,556,762 A | 9/1996 | Pinilla et al. | |
| 5,639,949 A | 6/1997 | Ligon et al. | |
| 5,689,633 A | 11/1997 | Cotner et al. | |
| 5,914,891 A | 6/1999 | Arkin et al. | |
| 5,930,154 A | 7/1999 | Thalhammer-Reyero | |
| 5,947,899 A | 9/1999 | Scollan et al. | |
| 6,132,969 A | 10/2000 | Stoughton et al. | |
| 6,165,709 A | 12/2000 | Friend et al. | |
| 6,200,803 B1 | 3/2001 | Roberts | |
| 6,221,597 B1 | 4/2001 | Roberts | |
| 6,302,302 B1 | 10/2001 | Albisetti | |
| 6,326,140 B1 | 12/2001 | Rine et al. | |
| 6,329,139 B1 | 12/2001 | Nova et al. | |
| 6,351,712 B1 | 2/2002 | Stoughton et al. | |
| 6,370,478 B1 | 4/2002 | Stoughton et al. | |
| 6,379,964 B1 | 4/2002 | Del Cardayre | |
| 6,500,710 B2 | 1/2005 | Thalhammer-Reyero | |
| 6,983,227 B1 | 1/2006 | Thalhammer-Reyero | |
| 6,902,692 B2 | 10/2006 | Palsson et al. | |
| 7,127,379 B2 | 10/2006 | Palsson et al. | |
| 2002/0012939 A1 | 1/2002 | Palsson | |
| 2002/0051998 A1 | 5/2002 | Schmidt et al. | |
| 2002/0168654 A1 | 11/2002 | Maranas et al. | |
| 2003/0059792 A1 | 3/2003 | Palsson et al. | |
| 2003/0113761 A1 | 6/2003 | Tan | |
| 2003/0224363 A1 | 12/2003 | Park et al. | |
| 2003/0233218 A1 | 12/2003 | Schilling | |
| 2004/0009466 A1 | 1/2004 | Maranas et al. | |
| 2004/0029149 A1 | 2/2004 | Palsson et al. | |
| 2004/0072723 A1 | 4/2004 | Palsson et al. | |
| 2006/0147899 A1 | 7/2006 | Famili et al. | |
| 2007/0111294 A1 | 5/2007 | Burgard et al. | |
| 2008/0176327 A1 | 7/2008 | Palsson et al. | |

FOREIGN PATENT DOCUMENTS

| | | |
|---|---|---|
| WO | WO 92/09300 | 6/1992 |
| WO | WO 00/46405 | 8/2000 |
| WO | WO 01/57775 | 8/2001 |
| WO | WO 02/055995 | 7/2002 |
| WO | WO 02/061115 | 8/2002 |
| WO | WO 03/106998 | 12/2003 |

OTHER PUBLICATIONS

Baily, "Complex Biology with No Parameters," *Nature Biotechnology*, 19:503-504, Nature Publishing Group (2001).

Berry, "Improving Production of Aromatic Compounds in *Escherichia coli* by Metabolic Engineering," *TIBTECH*, 14:250-256, Elsevier Science Ltd. (1996).

Bialy, "Living on the Edges," *Nature Biotechnology*, 19:111-112, Nature Publishing Group (2001).

Burgard and Maranas, "Probing the Performance Limits of the *Escherichia coli* Metabolic Network Subject to Gene Additions or Deletions," *Biotechnology and Bioengineering*, 74(5):364-375, John Wiley & Sons, Inc. (2001).

Edwards and Palsson, "Robustness Analysis of *Escherichia coli* Metabolic Network," *Biotechnol. Prog. 2000*, 16:927-939, American Chemical Society and American Institute of Chemical Engineers (2000).

Edwards and Palsson, "Systems Properties of the *Haemophilus influenzae* Rd Metabolic Genotype," *The Journal of Biological Chemistry*, 274(25):17410-17416, The American Society for Biochemistry and Molecular Biology, Inc. (1999).

(Continued)

*Primary Examiner* — Lori A Clow
(74) *Attorney, Agent, or Firm* — DLA Piper LLP (US)

(57) ABSTRACT

The present invention relates to methods for achieving an optimal function of a biochemical reaction network. The methods can be performed in silico using a reconstruction of a biochemical reaction network of a cell and iterative optimization procedures. The methods can further include laboratory culturing steps to confirm and possibly expand the determinations made using the in silico methods, and to produce a cultured cell, or population of cells, with optimal functions. The current invention includes computer systems and computer products including computer-readable program code for performing the in silico steps of the invention.

11 Claims, 17 Drawing Sheets

OTHER PUBLICATIONS

Edwards et al., "In silico Predictions of *Escherichia coli* Metabolic Capabilities are Consistent with Experimental Data," *Nature Biotechnology*, 19:125-130, Nature Publishing Group (2001).

Hasty et al., "Computational Studies of Gene Regulatory Networks: In Numero Molecular Biology," *Nat. Rev. Genet.*, 2:268-279, Macmillan Magazines Ltd (2001).

Heinrich and Rapoport, "Metabolic Regulation and Mathematical Models," *Prog. Biophys. Molec. Biol.*, 32:1-82, Pergamon Press (1977).

Heinrich et al., "Stoichiometric Analysis," *The Regulation of Cellular Systems*, xix:75-111, Chapman & Hall, New York (1996).

Sauer, "Evolutionary Engineering of Industrially Important Microbial Phenotypes," *Advances in Biochemical Engineering/Biotechnology*, 73:129-169, Springer-Verlag (2001).

Savageau, "Biochemical Systems Analysis," *J. Theoret. Biol.*, 25:365-369, (1969).

Stephanopoulos, "Metabolic Engineering," *Current Opinion in Biotechnology*, 5:196-200, Current Biology (1994).

Varner and Ramkrishna, "Mathematical Models of Metabolic Pathways," *Current Opinion in Biotechnology*, 10:146-150, Elsevier Science Ltd (1999).

Edwards & Palsson, "How Will Bioinformatics Influence Metabolic Engineering?", *Biotechnol. Bioeng.*, John Wiley & Sons, Inc., 58:162-169 (1998).

Edwards & Palsson, "Metabolic flux balance analysis and the in silico analysis of *Escherichia coli* K-12 gene deletions", *BMC Bioinformatics*, Oxford University Press, 1(1):1-10 (2000).

Edwards & Palsson, "The *Escherichia coli* MG1655 in silico metabolic genotype: Its definition, characteristics, and capabilities", *Poceedings of the National Academy of Sciences of USA*, 97(10):5528-5533 (2000).

Hatzimanikatis et al., "Analysis and Design of Metabolic Reaction Networks via Mixed-Integer Linear Optimization", *AIChE Journal*, 42(5):1277-1292 (1996).

Adamowicz et al., "Nutritional complementation of oxidative glucose metabolism in *Escherichia coli* via pyrroloquinoline quinone-dependent glucose dehydrogenase and the Entner-Doudoroff pathway," *Appl Environ Microbiol*, 57(7):2012-2015 (1991).

Akutsu, "Estimation Algorithm of Genetic Network," Mathmatical Science (Suri-Kagaku) Science 37(6)40-46 (19991.

Alberty, "Calculation of Biochemical Net Reactions and Pathways by Using Matrix Operations," *Biophys J*, 71(1):507-515 (1996).

Alm "Genomic-sequence comparison of two unrelated isolates of the human gastric pathogen *Helicobacter pylori*," *Nature*, 397(6715):176-80 (1999).

Alon et al., "Broad patterns of gene expression revealed by clustering analysis of tumor and normal colon tissues probed by oligonucleotide arrays," *Proc Natl Acad Sci U.S.A.*, 96(12):6745-6750 (1999).

Alter, et al., "Singular value decomposition for genome-wide expression data processing and modeling," *Proc Natl Acad Sci U.S.A.*, 97(18):10101-10106 (2000).

Altschul ,et al., "Gapped BLAST and PSI-BLAST: A New Generation of Protein Database Search Programs," *Nucl Acids Res*, 25(17):3389-3402 (1997).

Alves, et al., "Systemic properties of ensembles of metabolic networks: application of graphical and statistical methods to simple unbranched pathways," *Bioinformatics*, 16(6):534-547 (2000).

Andre, B, "An overview of membrane transport proteins in *Saccharomyces cerevisiae*," *Yeast*, 11(16):1575-1611 (1995).

Anonymous, "The yeast genome directory" *Nature*, 387(6632 Suppl):5 (1997).

Appel, et al., "A new generation of information retrieval tools for biologists: the example of the ExPASy WWW server," *Trends Biochem Sci*, 19(6):258-260 (1994).

Arigoni, et al., "A Genome-Based Approach for the Identification of Essential Bacterial Genes," *Nature Biotechnology*, 16(9):851-856 (1998).

Aristidou and Penttila, "Metabolic engineering applications to renewable resource utilization." Curr Opin in Biotech 11 (2)187-198 (2000).

Attanoos, et al., "Ileostomy polyps, adenomas, and adenocarcinomas," *Gut*, 37(6):840-844 (1995).

Baba, et al., "Construction of *Escherichia coli* K-12 in-frame, single-gene knockout mutants: the Keio collection," *Mol Syst Biol*, 2:2006-2008 (2006).

Bailey, J"Complex Biology With No Parameters," *Nat Biotechnol*, 19(6):503-504 (2001).

Bailey, T and Elkan, , "Fitting a mixture model by expectation maximization to discover motifs in biopolymers," *Proc Int Conf Intell Syst Mol Biol*, 2:28-36 (1994).

Bailey, T and Gribskov, M, "Combining evidence using p-values: application to sequence homology searches," *Bioinformatics*, 14(1):48-54 (1998).

Bairoch, A and Apweiler, R, "The SWISS-PROT Protein Sequence database and its supplement TrEMBL in 2000," *Nucleic Acids Res*, 28(1):45-48 (2000).

Ball, et al., "Integrating functional genomic information into the *Saccharomyces genome* database," *Nucleic Acids Res*, 28(1):77-80 (2000).

Baltz, et al., "DNA Sequence Sampling of the Streptococcus Pneumonia Genome to Identify Novel Targets for Antibiotic Development," *Microbial Drug Resistance*, 4(1):1-9 (1998).

Ban, et al., "Thymine and uracil catabolism in *Escherichia coli*," *J Gen Microbiol*, 73(2):267-272 (1972).

Bansal, "Integrating co-regulated gene-groups and pair-wise genome comparisons to automate reconstruction of microbial pathways," *Bioinformatics and Bioengineering Coference*, 209-216 (2001).

Bard, et al., "Sterol mutants of *Saccharomyces cerevisiae*: chromatographic analyses," *Lipids*, 12(8):645-654 (1977).

Baxevanis, A, "The Molecular Biology Database Collection: 2002 update," *Nucleic Acids Res*, 30:1-12 (2002).

Beard, et al., "Energy Balance for Analysis of Complex Metabolic Networks," Biophys J, 83(1):79-86 (2002).

Beckers, et al., "Large-Scale Mutational Analysis for the Annotation of the Mouse Genome," *Curr Opin Chem Biol*, 6(1)17-23 (2002).

Bell, et al., "Composition and functional analysis of the *Saccharomyces cerevisiae* trehalose synthase complex," *J Biol Chem.*, 273(50):33311-33319 (1998).

Benjamini Y and Hochberg, Y, "Controlling the false discovery rate: a practical and powerful approach to multiple testing," *J Roy Stat Soc Ser B (Methodological)*, 57:289-300 (1995).

Benson, et al., "GenBank," *Nucleic Acids Res*, 28(1):15-18 (2000).

Berry, A, "Improving production of aromatic compounds in *Escherichia coli* by metabolic engineering," *Trends Biotechnol*, 14(7):250-256 (1996).

Bialy, "Living on the Edges," Nat Biotechnol, 19(2):111-112 (2001).

Bianchi, P, and Zanella, A, *Blood Cells, Molecules, and Diseases*, 15:47-53 (2000).

Biaudet et al., "Micado—a network-oriented database for microbial genomes," *Comput Appl Biosci*, 13(4):431-438 (1997).

Birkholz, S., "Fumarate reductase of Helicobacter pylori—an immunogenic protein," *J Med Microbiol*, 41(1):56-62 (1994).

Birner, et al., "Roles of phosphatidylethanolamine and of its several biosynthetic pathways in *Saccharomyces cerevisiae*," *Mol Biol Cell*, 12(4):997-1007 (2001).

Blackstock, W and Weir, M, "Proteomics: quantitative and physical mapping of cellular proteins," *Trends Biotechnol*, 17(3):121-127 (1999).

Blattner et al., "The Complete Genome Sequence of *Escherichia coli* K-12," *Science*, 277(5331):1453-1474 (1997).

BMES/EMBS Conference, Proceedings of the First Joint, vol. 2, p. 1217 (1999).

Bochner, B, "New technologies to assess genotype-phenotype relationships," *Nat Rev Genet*, 4(4):309-314 (2003).

Boles, et al., "Identification and characterization of MAE 1 ,the *Saccharomy cescerevisiae* structural gene encoding mitochondrial malic enzyme," *J Bacteriol.*, 180(11):2875-2882 (1998).

Boles, et al., "A family of hexosephosphate mutases in *Saccharomyces cerevisia*," *Eur J Biochem*, 220(1):83-96 (1994).

Boles, et al., "Characterization of a glucose-repressed pyruvate kinase (Pyk2p) in *Saccharomyces cerevisiae* that is catalytically insensitive to fructose-1,6-bisphosphate," *J Bacteriol*, 179(9):2987-2993 (1997).

Bonarius, et al., "Flux Analysis of Underdetermined Metabolic Networks: The Quest for the Missing Constraints," *Trends Biotechnol*, 15(8):308-314 (1997).

Bonarius, et al., "Metabolic flux analysis of hybridoma cells in different culture media using mass balances," *Biotechnol Bioeng*, 50(3):299-318 (1996).

Bono, et al., "Reconstruction of amino acid biosynthesis pathways from the complete genome sequence," *Genome Research*, 8(3):203-210 (1998).

Bottomley, et al., "Cloning, sequencing, expression, purification and preliminary characterization of a type II dehydroquinase from *Helicobacter pylori*," *Biochem. J*, 319(Pt 2):559-565 (1996).

Bourot, S and Karst, F, "Isolation and characterization of the *Saccharomyces cerevisiae* SUT1 gene involved in sterol uptake," *Gene*, 165(1):97-102 (1995).

Burgard, A and Maranas, C, "Probing the Performance Limits of the *Escherichia coli* Metabolic Network Subject to Gene Additions or Deletions," *Biotechnol Bioeng*,74(5):364-375 (2001).

Burgard, A and Maranas, C, "Review of the Enzymes and Metabolic Pathways (EMP) Database," *Metab Eng*, 3(3):193-194(2) (2001).

Burgard, et al., "Minimal reaction sets for *Escherichia coli* metabolism under different growth requirements and uptake environments," *Biotechnol Prog*, 17(5):791-797 (2001).

Burgard, et al., "Optknock: a bilevel programming framework for identifying gene knockout strategies for microbial strain optimization," *Biotechnol Bioeng*, 84(6):647-657 (2003).

Burns, B, "Acetyl-CoA carboxylase activity in *Helicobacter pylori* and the requirement of increased CO2 for growth," *Microbiology*, 141(Pt 12):3113-3118 (1995).

Callis "Regulation of Protein Degradation." The Plant Cell 7:845-857 (1995).

Carrier and Keasling, "Investigating Autocatalytic Gene Expression Systems through Mechanistic Modeling." J Theor Biol 201(I):25-36 (1999).

Chartrain, et al., "Metabolic engineering and directed evotion for the production of pharmaceuticals," Curr Opin in Biotech 11(2):209-214 (2000).

Chadha et al., "Hybrid process for ethanol production from rice straw," *Acta Microbiol Immunol Hung*, 42(1):53-59 (1995).

Chadha, et al., "Simultaneous saccharification and fermentation of rice straw into ethanol," *Acta Microbiol Immunol Hung.*, 42(1):71-75 (1995).

Chalker, et al., "Systematic identification of selective essential genes in *Helicobacter pylori* by genome prioritization and allelic replacement mutagenesis," *J Bacteriol*, 183(4):1259-1268 (2001).

Chen, et al., "Characterization of the respiratory chain of *Helicobacter pylori*," *FEMS Immunol Med Microbiol*, 24(2):169-174 (1999).

Cherry, et al., "SGD: Saccharomyces Genome Database," *Nucleic Acids Res*, 26(1):73-79 (1998).

Christensen, B and Nielsen, J, "Metabolic network analysis. A powerful tool in metabolic engineering," *Advances in Biochemical Engineering/Biotechnology*, 66:209-231 (2000).

Ciriacy, M and Breitenbach, I, "Physiological effects of seven different blocks in glycolysis in *Saccharomyces cerevisiae*," *J Bacteriol*, 139(1):152-160 (1979).

Clarke, B, "Complete set of steady states for the general stoichiometric dynamical system," *J Chem Phys*, 75(10):4970-4979 (1981).

Clarke, B, "Stoichiometric network analysis," *Cell Biophys*, 12:237-253 (1988).

Clarke, B, *Stability of Complex Reaction Networks. Advances in Chemical Physics*, 43:1-125 (1980).

Clifton, D and Fraenkel, DG, "Mutant studies of yeast phosphofructokinase," *Biochemistry*, 21(8):1935-1942 (1982).

Clifton, et al., "Glycolysis mutants in *Saccharomyces cerevisiae*,"*Genetics*, 88(1):1-11 (1978).

Compan, I and Touati, D et al., "Anaerobic activation of arcA transcription in *Escherichia coli*: roles of Fnr and ArcA," *Mol Microbiol*, 11(5):955-964 (1994).

Costanzo et al., "YPD, PombePD and WormPD: model organism volumes of the BioKnowledge library, an integrated resource for protein information," *Nucleic Acids Res*, 29(1):75-9 (2001).

Cotter et al., "Aerobic regulation of cytochrome d oxidase (cydAB) operon expression in *Escherichia coli*: roles of Fnr and ArcA in repression and activation," *Mol Microbiol*, 25(3):605-615 (1997).

Cover, T and Blaser, M, "*Helicobacter pylori* infection, a paradigm for chronic mucosal inflammation: pathogenesis and implications for eradication and prevention," *Adv Intern Med*, 41:85-117 (1996).

Covert M and Palsson, B, "Constraints-based models: regulation of gene expression reduces the steady-state solution space" *J Theor Biol*, 216 (2003).

Covert M and Palsson, B, "Transcriptional regulation in constraints-based metabolic models of *Escherichia coli*," *J Biol Chem*, 277(31):28058-28064 (2002).

Cupp, JR and McAlister-Henn, L, "Cloning and Characterization of the gene encoding the IDH1 subunit of NAD(+)-dependent isocitrate dehydrogenase from *Saccharomyces cerevisiae*," *J Biol Chem*, 267(23):16417-16423 (1992).

Dafoe, et al., "In Silico Knowledge Discovery Biomedical databases," Proceedings of the SPIE Fifth Workshop on Neural Networks, San Francisco, Nov. 7-10, 1993.

D'Haeseleer, et al., "Genetic network inference: from co-expression clustering to reverse engineering," *Bioinformatics*, 16(8):707-726 (2000).

Danchin, A, "Comparison Between the *Escherichia coli* and *Bacillus subtilis* Genomes Suggests That a Major Function of Polynucleotide Phosphorylase is to Synthesize CDP," *DNA Research*, 4(1):9-18 (1997).

Dandekar, et al., "Pathway Alignment: Application to the Comparative Analysis of Glycolytic Enzymes," *Biochem J*, 343(Pt 1):115-124 (1999).

Dantigny, et al., "Transition rate kinetics from ethanol oxidation to glucose utilisation within a structured model of baker's yeast," *Appl Microbiol Biotechnol*, 36:352-357 (1991).

Datsenko, K and Wanner, B, "One-step inactivation of chromosomal genes in *Escherichia coli* K-12 using PCR products," *Proc Natl Acad Sci U.S.A.*, 97(12):6640-6645 (2000).

Daum, et al., "Biochemistry, cell biology and molecular biology of lipids of *Saccharomyces cerevisiae*," *Yeast*, 14(16):1471-1510 (1998).

Daum, et al., "Systematic analysis of yeast strains with possible defects in lipid metabolism," *Yeast*, 15(7):601-614 (1999).

Dauner, et al., "*Bacillus subtilis* Metabolism and Energetics in Carbon-Limited and Excess-Carbon Chemostat Culture," *J Bacteriol*, 183(24):7308-7317 (2001).

Dauner, et al., "Metabolic Flux Analysis with a Comprehensive Isotopomer Model in *Bacillus subtilis*," *Biotechnol Bioeng*, 76(2):144-156 (2001).

Dauner, M and Sauer, U, "Stoichiometric Growth Model for Riboflavin-Producing *Bacillus subtilis*," *Biotechnol Bioeng*, 76(1):132-143 (2001).

de Jong, H, "Modeling and simulation of genetic regulatory systems: a literature review," *J Comput Biol*, 9(1):67-103 (2002).

De Reuse, et al., "The *Helicobacter pylori* ureC gene codes for a phosphoglucosamine mutase," *J Bacteriol*, 179(11):3488-3493 (1997).

Delgado and Liao, "Identifying Rate-Controlling Enzymes in Metabolic Pathways without Kinetic Parameters," *Biotechnol Prog*, 7:15-20 (1991).

Demain et al., "Cellulase, clostridia, and ethanol," *Microbiol Mol Biol Rev*, 69(1):124-154 (2005).

Department of Energy, *Breaking the Biological Barriers to Cellulosic Ethanol* (2006).

DeRisi, et al, "Exploring the Metabolic and Genetic Control of Gene Expression on a Genomic Scale," *Science*, 278(5338):680-686 (1997).

DeRisi, et al, "Use of cDNA microarray to analyse gene expression patters in human cancer," Nat Gene 14:457-460 (1996).

Devine, K, "The *Bacillus subtilis* Genome Project: Aims and Progress," *Trends Biotechnol*, 13(6):210-216 (1995).

Dickson, R, "Sphingolipid functions in *Saccharomyces cerevisiae*: comparison to mammals," *Annu Rev Biochem*, 67:27-48 (1998).

Dickson, et al., "Serine palmitoyltransferase," *Methods Enzymol*, 311:3-9 (2000).

DiRusso, C and Black, P, "Long-chain fatty acid transport in bacteria and yeast. Paradigms for defining the mechanism underlying this protein-mediated process," *Mol Cell Biochem*, 192(1-2):41-52 (1999).

Dooley, et al., "An all D-amino acid opiod peptide with central analgesic activity from a combinatorial library," *Science*, 266(5193):2019-2022 (1994).

Edwards, et al., "Characterizing the Metabolic Phenotype: A Phenotype Phase Plane Analysis," *Biotech Bioeng*, 77(1):27-36 (2002).

Edwards, J and Palsson, B, "How Will Bioinformatics Influence Metabolic Engineering," *Biotechnol Bioeng*, 58(2-3):162-169 (1998).

Edwards, J and Palsson, B, "Systems properties of the Haemophilus influenzae Rd metabolic genotype," *J Biol Chem*, 274(25):17410-17416 (1999).

Edwards, J, and Palsson, B, "Metabolic flux balance analysis and the in silico analysis of *Escherichia colia* K-12 gene deletions," *BMC Bioinformatics*, 1:1-10 (2000).

Edwards, et al., "Genomically Based Comparative Flux Balance Analysis of *Escherichia coli* and Haemophilus Influenza," Abstract of Papers, *American Chemical Society*, 213(1-3):BIOT 50. San Francisco (13-17, 1997).

Eisen, et al., "Cluster analysis and display of genome-wide expression patterns," *Proc Natl Acad Sci U.S.A.*, 95:14863-14868 (1998).

Eisenberg, et al., "Protein Function in the Post-Genomic Era," *Nature*, 405(6788):823-826 (2000).

Ermolaeva, et al., "Prediction of Operons in Microbial Genomes," *Nucl Acids Research*, 29(5):1216-1221 (2001).

Everett, et al., "Pendred Syndrome is Caused by Mutations in a Putative Sulphate Transporter Gene (PDS)," *Nat Genet*, 17:411-422 (1997).

Feist, AM and Palsson, BO, "The growing scope of applications of genome-scale metabolic reconstructions using *Escherichia coli*," *Natural Biotech*, 26(6):659-667 (2008).

Fell, D and Small, J, "Fat Synthesis in Adipose Tissue. An Examination of Stoichiometric Constraints," *Biochem J*, 238(3):781-786 (1986).

Fiehn, O, "Metabolomics—the link between genotypes and phenotypes," *Plant Mol Biol*, 48(1-2):155-171 (2002).

Finel, M, "Does NADH play a central role in energy metabolism in *Helicobacter pylori*?," *Trends Biochem Sci*, 23(11):412-413 (1998).

Fiorelli, et al., "Chronic non-spherocytic haemolytic disorders associated with glucose-6-phosphate dehydrogenase variants," *Bailliere's Clinical Haematology*, 13:39-55 (2000).

Fleischmann, R, "Whole-genome random sequencing and assembly of Haemophilus influenzae Rd," *Science*, 269(5223):496-512 (1995).

Flikweert, et al., "Pyruvate decarboxylase: an indispensable enzyme for growth of *Saccharomyces cerevisiae* on glucose," *Yeast*, 12(3):247-257 (1996).

Forst, "Network genomics—A Novel approach for the analysis of biological systems in the post-genomic era," *Molecular Biology Reports*, 29(3):265-280 (2002).

Forster, et al., "Large-scale evaluation of in silico gene deletions in *Saccharomyces cerevisiae*," *Omics*, 7(2)193-202 (2003).

Fraenkel, D, "The accumulation of glucose 6-phosphate from glucose and its effect in an *Escherichia coli* mutant lacking phosphoglucose isomerase and glucose 6-phosphate dehydrogenase" *J Biol Chem*, 243(24):6451-6457 (1968).

Fraser, et al., "Microbial genome sequencing," *Nature*, 406:799-803 (2000).

Fromont-Racine, et al., "Toward a functional analysis of the yeast genome through exhaustive two-hybrid screens," *Nat Genet*, 16(3):277-282 (1997).

Fukuchi, et al., "Isolation, overexpression and disruption of a *Saccharomyces cerevisiae* YNK gene encoding nucleoside diphosphate kinase," *Genes*, 129(1):141-146 (1993).

Gaasterland, T. and Selkov, E., "Reconstruction of Metabolic Networks Using Incomplete Information," *Proc Int Conf Intell Syst Mol Biol*, 3:127-135 (1995).

Galperin, M and Brenner, S, "Using Metabolic Pathway Databases for Functional Annotation," *Trends Genet*, 14(8):332-333 (1998).

Gancedo, C and Delgado, M, "Isolation and characterization of a mutant from *Saccharomyces cerevisiae* lacking fructose 1,6-bisphosphatase," *Eur J Biochem*, 139:651-655 (1984).

Gangloff, et al., "Molecular cloning of the yeast mitochondrial aconitase gene (ACO1) and evidence of a synergistic regulation of expression by glucose plus glutamate," *Mol Cell Biol*, 10(7):3551-3561 (1990).

Ge, et al., "Cloning and functional characterization of *Helicobacter pylori* fumarate reductase operon comprising three structural genes coding for subunits C, A and B," *Gene*, 204(1-2):227-234 (1997).

Glasner, et al., "ASAP, a systematic annotation package for community analysis of genomes," *Nucleic Acids Res*, 31(1):147-151 (2003).

Goffeau, A, "Four years of post-genomic life with 6000 yeast genes," *FEBS Lett*, 480(1):37-41 (2000).

Goryanin, et al., "Mathematical simulation and analysis of cellular metabolism and regulation," *Bioinformatics*, 15(9):749-758 (1999).

Goto, et al., "LIGAND database for enzymes, compounds and reactions," *Nucleic Acids Res*, 27(1):377-379 (1999).

Goto, et al., "LIGAND: chemical database for enzyme reactions," *Bioinformatics*, 14(7):591-599 (1998).

Grewal, et al., "Computer Modelling of the Interaction Between Human Choriogonadotropin and Its Receptor," *Protein Engineering*, 7(2):205-211 (1994).

Griffin, et al., "Complementary profiling of gene expression at the transcriptome and proteome levels in *Saccharomyces cerevisiae*," *Mol Cell Proteomics*, 1:323-333 (2002).

Grundy, et al., "Regulation of the *Bacillus subtilis* acetate kinase gene by CcpA." *J Bacteriol*, 175(22):7348-7355 (1993).

Guelzim et al., "Topological and causal structure of the yeast transcriptional regulatory network," *Nat Genet*, 31(1):60-63 (2002).

Guetsova et al., "The isolation and characterization of *Saccharomyces cerevisiae* mutants that constitutively express purine biosynthetic genes," *Genetics*, 147(2):383-397 (1997).

Hardison, et al., "Globin Gene Server: A Prototype E-Mail Database Server Featuring Extensive Multiple Alignments and Data Compilation for Electronic Genetic Analysis," *Genomics*, 21(2):344-353 (1994).

Hartig, et al., "Differentially regulated malate synthase genes participate in carbon and nitrogen metabolism of *S. cerevisiae*," *Nucleic Acids Res*, 20(21):5677-5686 (1992).

Hasty, et al., "Computational Studies of Gene Regulatory Networks: In Numero Molecular Biology," *Nat Rev Genet*, 2(4):268-279 (2001).

Hata, et al., "Characterization of a *Saccharomyces cerevisiae* mutant, N22, defective in ergosterol synthesis and preparation of [28-14C]ergosta-5,7-dien-3 beta-ol with the mutant," *J Biochem*, 94(2):501-510 (1983).

Hatzimanikatis, et al., "Analysis and Design of Metabolic Reaction Networks Via Mixed-Interger linear Optimization," *AIChE Journal*, 42(5):1277-1292 (1996).

Hazell, et al., "How *Helicobacter pylori* works: an overview of the metabolism of *Helicobacter pylori*," *Helicobacter*, 2(1):1-12 (1997).

Heijnen, et al., "Application of balancing methods in modeling the penicillin fermentation," *Microbiol Biochem*, 21:1-48 (1979).

Heinisch, et al., "Investigation of two yeast genes encoding putative isoenzymes of phosphoglycerate mutase," *Yeast*, 14(3):203-213 (1998).

Heinrich, et al., "Metabolic regulation and mathematical models," *Prog Biophys Mol Biol*, 32(1):1-82 (1977).

Henriksen, et al., "Growth energetics and metabolism fluxes in continuous cultures of *Penicillium chrysogenum*," *J of Biotechnol*, 45(2):149-164 (1996).

Heyer, et al., "Exploring expression data: identification and analysis of coexpressed genes," *Genome Res*, 9(11):1106-1115 (1999).

Holter, et al., "Dynamic modeling of gene expression data," *Proc Natl Acad Sci U.S.A.*, 98(4):1693-1698 (2001).

Holter, et al., "Fundamental patterns underlying gene expression profiles: simplicity from complexity," *Proc Natl Acad Sci U.S.A.*, 97:8409-9414 (2000).

Houghten, R, "Generation and use of synthetic peptide combinatorial libraries for basic research and drug discovery," *Nature*, 354(6348):84-86 (1991).

Hughes, et al., "Functional discovery via a compendium of expression profiles," *Cell*, 102(1):109-126 (2000).

Hughes, et al., "*Helicobacter pylori* porCDAB and oorDABC genes encode distinct pyruvate: flavodoxin and 2-oxoglutarate:acceptor oxidoreductases which mediate electron transport to NADP," *J Bacteriol*, 180(5):1119-1128 (1998).

Ideker, et al., "Integrated Genomic and Proteomic Analyses of a Systematically Perturbed Metabolic Network," *Science*, 292(5518):929-934 (2001).

Ince, J and Knowles, C, "Ethylene formation by cell-free extracts of *Escherichia coli*," *Arch Microbiol*, 146(2):151-158 (1986).

Ishii, et al., "DBTBS: a database of *Bacillus subtilis* promoters and transcription factors," *Nucleic Acids Res*, 29(1):278-280 (2001).

Iyer, et al., "Genomic binding sites of the yeast cell-cycle transcription factors SBF and MBF," *Nature*, 409(6819):533-538 (2001).

Jamshidi, et al., "Dynamic simulation of the human red blood cell metabolic network," *Bioinformatics*, 17(3):286-287 (2001).

Jamshidi, et al., "In silico model-driven assessment of the effects of single nucleotide polymorphins (SNPs) on human red blood cell-metabolism," Genome Research, 12(11):1687-1692 (2002).

Jenkins, L and Nunn, W, "Genetic and molecular characterization of the genes involved in short-chain fatty acid degradation in *Escherichia coli*: the ato system," *J Bacteriol*, 169(1):42-52 (1987).

Jenssen, et al., "A Literature Network of Human Genes for High-Throughput Analysis of Gene Expression," *Nat Genet*, 28(1):21-28 (2001).

Jorgensen, et al., "Metabolic flux distributions in *Penicillium chrysogenum* during fed-batch cultivations." *Biotechnol Bioeng*, 46(2):117-131 (1995).

Joshi, A and Palsson, B, "Metabolic dynamics in the human red cell. Part I—A comprehensive kinetic model," *J Theor Biol*, 141(4):515-528 (1989).

Juty, et al., "Simultaneous Modeling of Metabolic, Genetic, and Product-Interaction Networks," *Briefings in Bioinformatics*, 2(3):223-232 (2001).

Kanehisa, M and Goto, S, "Kyoto Encyclopedia of Genes and Genomes database (KEGG)," *Nucleic Acids Res*, 28(1):27-30 (2000).

Karp, P, "An ontology for biological function based on molecular interactions," *Bioinformatics*, 16(3):269-285 (2000).

Karp, P, "Metabolic Databases," *Trends Biochem Sci*, Elsevier Publication, Cambridge, 23(3):114-116 (1998).

Karp, et al., "Eco Cyc: encyclopedia of *Escherichia coli* genes and metabolism" *Nucleic Acids Res*, 27(1):55-58 (1999).

Karp, et al., "EcoCyc: Encyclopedia of *Escherichia coli* Genes and Metabolism," *Nucleic Acids Research*, 25(1):43-50 (1997).

Karp, et al., "HinCyc: A knowledge base of the complete genome and metabolic pathways of H. influenzae," *Proc Int Conf Intell Syst Mol Biol*, 4:116-124 (1996).

Karp, et al., "Integrated pathway-genome databases and their role in drug discovery," *Trends Biotechnol*, 17(7):275-281 (1999).

Karp, et al., "The EcoCyc and MetaCyc databases," *Nucleic Acids Resarch*, 28(1):56-59 (2000).

Kather, et al., "Another unusual type of citric acid cycle enzyme in *Helicobacter pylori*: the malate:quinone oxidoreductase," *J Bacteriol*, 182(11):3204-3209 (2000).

Keating, et al., "An ethanologenic yeast exhibiting unusual metabolism in the fermentation of lignocellulosic hexose sugars," *J Ind Microbiol Biotechnol*, 31(5):235-244 (2004).

Kelly, D, "The physiology and metabolism of the human gastric pathogen *Helicobacter pylori*," *Adv Microb Physiol*, 40:137-189 (1998).

Kim et al., "*Saccharomyces cerevisiae* contains two functional citrate synthase genes," *Mol Cell Biol*, 6(6):1936-1942 (1986).

Kirkman, et al., "Red cell NADP+ and NADPH in glucose-6-phosphate dehydrogenase deficiency," *Journal of Clinical Investigation*, 55(4):875-878 (1975).

Kremling, et al., "The organization of metabolic reaction networks. III. Application for diauxic growth on glucose and lactose," *Metab Eng*, 3(4):362-379 (2001).

Kunst, et al., "The Complete Genome Sequence of the Gram-positive Bacterium *Bacillus subtilus*," *Nature*, 390(6557):249-256 (1997).

Lacroute, F, "Regulation of pyrimidine biosynthesis in *Saccharomyces cerevisiae*" *J Bacteriol*, 95(3):824-832 (1968).

Latif, F and Rajoka, MI, "Production of ethanol and xylitol from corn cobs by yeasts," *Bioresour Technol*, 77(1):57-63 (2001).

Lendenmann, U and Egli, T, "Is *Escherichia coli* growing in glucose-limited chemostat culture able to utilize other sugars without lag?," *Microbiology*, 141(Pt 1):71-78 (1995).

Leyva-Vasquez, M and Setlow, P, "Cloning and nucleotide sequences of the genes encoding triose phosphate isomerase, phosphoglycerate mutase, and enolase from *Bacillus subtilis*," *J Bacteriol*, 176(13):3903-3910 (1994).

Li, C and Wong, W, "Model-based analysis of oligonucleotide arrays: expression index computation and outlier detection," *Proc Natl Acad Sci U.S.A.*, 98(1):31-36 (2001).

Liao, et al., "Pathway Analysis, Engineering, and Physiological Considerations for Redirecting Central Metabolism," *Biotechnol Bioeng*, 52(1):129-140 (1996).

Liao, J and Oh, M, "Toward predicting metabolic fluxes in metabolically engineered strains," *Metab Eng*,1(3):214-223 (1999).

Link, et al., "Methods for generating precise deletions and insertions in the genome of wild-type *Escherichia coli*: Application to open reading frame characterization," *J Bacteriol*, 179(20):6228-6237 (1997).

Loftus, et al., "Isolation, characterization, and disruption of the yeast gene encoding cytosolic NADP-specific isocitrate dehydrogenase," *Biochemistry*, 33(32):9661-9667 (1994).

Lopez, et al., "The yeast inositol monophosphatase is a lithium- and sodium-sensitive enzyme encoded by a non-essential gene pair," *Mol Microbiol*, 31(4):1255-1264 (1999).

Mahadevan, R and Schilling, C, "The effects of alternate optimal solutions in constraint-based genome-scale metabolic models," *Metab Eng*, 5(4):264-276 (2003).

Maier, et al., "Hydrogen uptake hydrogenase in *Helicobacter pylori*," *FEMS Microbiol Lett*, 141(1):71-76 (1996).

Majewski, R and Domach, M, "Simple Constrained-Optimization View of Acete Overflow in *E. Coli*," *Biotechnol Bioeng*, 35(7):732-738 (1990).

Marcelli, et al., "The respiratory chain of *Helicobacter pylori*: identification of cytochromes and the effects of oxygen on cytochrome and menaquinone levels," *FEMS Microbiol Lett*, 138(1):59-64 (1996).

Marshall, B and Warren, J, "Unidentified curved bacilli in the stomach of patients with gastritis and peptic ulceration," *Lancet*, 1(8390):1311-1315 (1984).

McAdams, H and Arkin, A, "Simulation of Prokaryotic Genetic Circuits," *Annual Review of Biophysics and Biomolecular Structure*, 27:199-224 (1998).

McAdams, H and Shapiro, L, "Circuit simulation of genetic networks." *Science*, 269(5224):650-656 (1995).

McAlister-Henn, L and Thompson, L, "Isolation and expression of the gene encoding yeast mitochondrial malate dehydrogenase," *J Bacteriol*, 169(11):5157-5166 (1987).

McGee, D, "*Helicobacter pylori* rocF is required for arginase activity and acid protection in vitro but is not essential for colonization of mice or for urease activity," *J Bacteriol*, 165(1):65-76 (1998).

Meldrum, D, "Automation for genomics, part one: preparation for sequencing," *Genome Res*, 10(8):1081-1092 (2000).

Mendes, P and Kell, D, "Non-linear optimization of biochemical pathways: Applications to metabolic engineering and parameter estimation," Bioinformatics, 14(10):869-883 (1998).

Mendz, et al., "Characterisation of glucose transport in *Helicobacter pylori*," *Biochim Biophys Acta*, 1244(2-3):269-276 (1995).

Mendz, et al., "Characterization of fumarate transport in *Helicobacter pylori*," *J Membr Biol*, 165(1):65-76 (1998).

Mendz et al., "De novo synthesis of pyrimidine nucleotides by *Helicobacter pylori*," *J Appl Bacteriol*, 77(1):1-8 (1994).

Mendz, "Fumarate reductase: a target for therapeutic intervention against *Helicobacter pylori*," *Arch Biochem Biophys*, 321(1):153-159 (1995).

Mendz, et al., "Glucose utilization and lactate production by *Helicobacter pylori*," *J Gen Microbiol*, 139(12):3023-3028 (1993).

Mendz, et al., "In situ characterization of *Helicobacter pylori* arginase," *Biochim Biophys Acta*, 1388(2):465-477 (1998).

Mendz, et al., "Purine metabolism and the microaerophily of *Helicobacter pylori*,"*Arch Microbiol*, 168(6):448-456 (1997).

Mendz, et al., "The Entner-Doudoroff pathway in *Helicobacter pylori*," *Arch Biochem Biophys*, 312(2):349-356 (1994).

Mendz, G and Hazell S, "Aminoacid utilization by *Helicobacter pylori*," *Int J Biochem Cell Biol*, 27(10):1085-1093 (1995).

Mendz, G and Hazell, S, "Fumarate catabolism in *Helicobacter pylori*," *Biochem Mol Biol Int*, 31(2):325-332 (1993).

Mendz, G and Hazell, S, "Glucose phosphorylation in *Helicobacter pylori*," *Arch Biochem Biophys*, 300(1):522-525 (1993).

Mendz, G et al., "Pyruvate metabolism in *Helicobacter pylori*," *Arch Microbiol*, 162(3):187-192 (1994).

Mendz, et al., "Glucose utilization and lactate production by *Helicobacter pylori*," J Gen Microbiol, 139(12):3023-3028 (1993).

Mendz, G et al., "Salvage synthesis of purine nucleotides by *Helicobacter pylori*," *J Appl Bacteriol*, 77(6):674-681 (1994).

Mewes, et al., "MIPS: A database for genomes and protein sequences," *Nucleic Acids Research*, 30(1):31-34 (2002).

Mitchell, A, "The GLN1 locus of *Saccharomyces cerevisiae* encodes glutamine synthetase," *Genetics*, 111(2):243-258 (1985).

Moszer, I, "The Complete Genome of *Bacillus subtilis*: From Sequence Annotation to Data Management and Analysis," *FEBS Lett*, 430(1-2):28-36 (1998).

Moszer, et al., "SubtiList: the reference database for the *bacillus subtilis* genome," *Nucleic Acids Res*, 30(1):62-65 (2002).

Mulquiney, P and Kuchel, P, "Model of 2,3-bisphosphoglycerate metabolism in the human erythrocyte based on detailed enzyme kinetic equations: computer simulation and metabolic control analysis," *Biochem J*, 342(Pt 3):597-604 (1999).

Murray, M and Greenberg, M, "Expression of yeast INM1 encoding inositol monophosphatase is regulated by inositol, carbon source and growth stage and is decreased by lithium and valproate," *Mol Microbiol*, 36(3):651-661 (2000).

Nedenskov, "Nutritional requirements for growth of *Helicobacter pylori*," *Appl Environ Microbiol*, 60(9):3450-3453 (1994).

Nissen et al., "Expression of a cytoplasmic transhydrogenase in *Saccharomyces cerevisiae* results in formation of 2-oxoglutarate due to depletion of the NADPH pool," *Yeast*, 18(1):19-32 (2001).

Nissen et al., "Flux distributions in anaerobic, glucose-limited continuous cultures of *Saccharomyces cerevisiae*," *Microbiology*, 143(Pt 1):203-218 (1997).

Ogasawara, N,"Systematic function analysis of *Bacillus subtilis* genes," *Res Microbiol*, 151(2):129-134 (2000).

Ogata, et al., "KEGG: Kyoto Encyclopedia of Genes and Genomes," *Nucleic Acids Res*, 27(1):29-34 (1999).

Oh, M and Liao, J, "Gene expression profiling by DNA microarrays and metabolic fluxes in *Escherichia coli*," *Biotech Prog*, 16:278-286 (2000).

Olsson, et al., "Separate and simultaneous enzymatic hydrolysis and fermentation of wheat hemicellulose with recombinant xylose utilizing *Saccharomyces cerevisiae*," *Appl Biochem Biotechnol*, 129-132:117-129 (2006).

Otto, et al., "A mathematical model for the influence of fructose 6-phosphate, ATP, potassium, ammonium and magnesium on the phosphofructokinase from rat erythrocytes," *Eur J Biochem*, 49(1):169-178 (1974).

Ouzounis, C and Karp, P, "Global Properties of the Metabolic Map of *Escherichia coli*," *Genome Res*, 10(4):568-576 (2000).

Overbeek, et al., "WIT: Integrated System for High-Throughput Genome Sequence Analysis and Metabolic Reconstruction" *Nucleic Acids Res*, 28(1):123-125 (2000).

Overkamp, et al., "In vivo analysis of the mechanisms for oxidation of cytosolic NADH by *Saccharomyces cerevisiae* mitochondria," *J Bacteriol*, 182(10):2823-2830 (2000).

Ozcan, S, Freidel, K, Leuker, A. & Ciriacy, M., "Glucose uptake and catabolite repression in dominant HTR1 mutants of *Saccharomyces cerevisiae*," *J Bacteriol*, 175(17):5520-5528 (1993).

Pallotta, et al., "*Saccharomyces cerevisiae* mitochondria can synthesise FMN and FAD from externally added riboflavin and export them to the extramitochondrial phase," *FEBS Lett*, 428(3):245-249 (1998).

Palmieri, et al., "Identification and functions of new transporters in yeast mitochondria," *Biochim Biophys Acta*, 1459(2-3):363-369 (2000).

Palmieri, et al., "Identification of the yeast ACR1 gene product as a succinate-fumarate transporter essential for growth on ethanol or acetate," *FEBS Lett*, 417(1):114-118 (1997).

Palmieri, et al., "Identification of the yeast mitochondrial transporter for oxaloacetate and sulfate," *J Biol Chem*, 274(32):22184-22190 (1999).

Palmieri, et al., "Yeast mitochondrial carriers: bacterial expression, biochemical identification and metabolic significance," *J Bioenerg Biomembr*, 32(1):67-77 (2000).

Palsson, "The Challenges of in Silico Biology," *Nat Biotechnol*, 18(11):1147-1150 (2000).

Palsson, "What Lies Beyond Bioinformatics," *Nat Biotechnol*, 15:3-4 (1997).

Papin et al., "The genome-scale metabolic extreme pathway structure in Haemophilus influenzae shows significant network redundancy," *J Theor Biol*, 215(1):67-82 (2002).

Parks, "Metabolism of sterols in yeast," *CRC Crit Rev Microbiol*, 6(4):301-341 (1978).

Parks et al., "Use of sterol mutants as probes for sterol functions in the yeast, *Saccharomyces cerevisiae*," *Crit Rev Biochem Mol Biol*, 34(6):399-404 (1999).

Patel, B and West, T, ",Degradation of the pyrimidine bases uracil and thymine by *Escherichia coli* B" *Microbios*, 49(199):107-113 (1987).

Paulsen, et al., "Unified inventory of established and putative transporters encoded within the complete genome of *Saccharomyces cerevisiae*," *FEBS Lett*, 430(1-2):116-125 (1998).

Pearson, et al., "Comparison of DNA Sequences With Protein Sequences," *Genomics*, 46(1):24-36 (1997).

Pennisi, "Laboratory Workhouse Decoded," *Science*, 277(5331):1432-1434 (1997).

Persson, et al., "Phosphate permeases of *Saccharomyces cerevisiae*: structure, function and regulation," *Biochim Biophys Acta*, 1422(3):255-272 (1999).

Peterson, et al., "The Comprehensive Microbial Resource," *Nucleic Acids Res*, 29(1):123-125 (2001).

Pharkya, et al., "Exploring the overproduction of amino acids using the bilevel optimization framework OptKnock," *Biotechnol Bioeng*, 84(7):887-899 (2003).

Phelps, et al., "Metabolomics and microarrays for improved understanding of phenotypic characteristics controlled by both genomics and environmental constraints," *Curr Opin Biotechnol*, 13(1):20-24 (2002).

Pitson, et al., "The tricarboxylic acid cycle of *Helicobacter pylori*," *Eur J Biochem*, 260(1):258-267 (1999).

Pramanik, J and Keasling, J, "Stoichiometric Model of *Escherichia coli* Metabolism: Incorporation of Growth-Rate Dependent Biomass Composition and Mechanistic Energy Requirements," *Biotechnol Bioeng*, 56(4):398-421 (1997).

Price, et al., "Determination of redundancy and systems properties of the metabolic network of *Helicobacter pylori* using genome-scale extreme pathway analysis," *Genome Res*, 12(5):760-769 (2002).

Price, et al., "Genome-scale models of microbial cells: evaluating the consequences of constraints," *Nat Rev Microbiol*, 2(11):886-897 (2004).

Price, et al., "Network-based analysis of metabolic regulation in the human red blood cell," *J Theor Biol*, 225(2):185-194 (2003).

Przybyla-Zawislak, et al., "Genes of succinyl-CoA ligase from *Saccharomyces cerevisiae*," *Eur J Biochem*, 258(2):736-743 (1998).

Qian, et al., "Ethanol production from dilute-Acid softwood hydrolysate by co-culture," *Appl Biochem Biotechnol*, 134(3):273-284 (2006).

Reed, et al., "An expanded genome-scale model of *Escherichia coli* K-12 (iJR904 GSM/GPR)," *Genome Biol*, 4(9):R54 (2003).

Reed, J and Palsson, B, "Thirteen years of building constraint-based in silico models of *Escherichia coli*" *J Bacteriol*, 185(9):2692-2699 (2003).

Regenberg et al., "Substrate specificity and gene expression of the amino-acid permeases in *Saccharomyces cerevisiae*," *Curr Genet*, 36(6):317-328 (1999).

Remize, et al., "Engineering of the pyruvate dehydrogenase bypass in *Saccharomyces cerevisiae*: role of the cytosolic Mg(2+) and mitochondrial K(+) acetaldehyde dehydrogenases Ald6p and Ald4p in acetate formation during alcoholic fermentation," *Appl Environ Microbial*, 66(8):3151-3159 (2000).

Ren, et al., "Genome-wide location and function of DNA binding proteins," *Science*, 290(5500):2306-2309 (2000).

Repetto, B and Tzagoloff, A, "In vivo assembly of yeast mitochondrial alpha-ketoglutarate dehydrogenase complex," *Mol Cell Biol*, 11(8):3931-3939 (1991).
Reynolds, D and Penn, C, "Characteristics of *Helicobacter pylori* growth in a defined medium and determination of its amino acid requirements," *Microbiology*, 140(Pt 10):2649-2656 (1994).
Rhee, et al., "Activation of gene expression by a ligand-induced conformational change of a protein-DNA complex," *J Biol Chem*, 273(18):11257-11266 (1998).
Romero, P and Karp, P, "Nutrient-Related Analysis of Pathway/Genome Databases," *Pac Symp Biocomput*, 471-482 (2001).
Saier, M, "Genome sequencing and informatics: new tools for biochemical discoveries," *Plant Physiol*, 117(4):1129-1133 (1998).
Salgado, et al., "RegulonDB (version 3.2): transcriptional regulation and operon organization in *Escherichia coli* K-12," *Nucleic Acids Res*, 29(1):72-74 (2001).
Salmon, et al., "Global gene expression profiling in *Escherichia coli* K12. The effects of oxygen availability and FNR," *J Biol Chem*, 278(32):29837-29855 (2003).
Sauer, et al., "Metabolic Capacity of *Bacillus subtilis* for the Production of Purine Nucleosides, Riboflavin, and Folic Acid," *Biotechnol Bioeng*, 59(2):227-238 (1998).
Sauer, et al., "Metabolic flux ratio analysis of genetic and environmental modulations of *Escherichia coli* central carbon metabolism," *J Bacteriol*, 181(21):6679-6688.
Sauer, U and Bailey, J, "Estimation of P-to-O Ratio in *Bacillus subtilis* and Its Influence on Maximum Riboflavin Yield," *Biotechnol Bioeng*, 64(6):750-754 (1999).
Sauer, U, "Evolutionary Engineering of Industrially Important Microbial Phenotypes," *Adv in Biochem Eng Biotechnol*, 73:129-169 (2001).
Savageau, M, "Biochemical systems analysis. I. Some mathematical properties of the rate law for the component enzymatic reactions,"*J Theor Biol*, 25(3):365-369 (1969).
Savinell, J and Palsson, B, "Network Analysis of Intermediary Metabolism using Linear Optimization. II. Interpretation of Hybridoma Cell Metabolism," *J Theor Biol*, 154:455-473 (1992).
Savinell, J and Palsson, B, "Network Analysis of Intermediary Metabolism using Linear Optimization. I. Development of Mathematical Formalism," *J Theor Biol*, 154:421-454 (1992).
Schaaff-Gerstenschlager, I and Zimmermann, FK, "Pentose-phosphate pathway in *Saccharomyces cerevisiae*: analysis of deletion mutants for transketolase, transaldolase, and glucose 6-phosphate dehydrogenase," *Curr Genet*, 24(5):373-376 (1993).
Schaff, et al., "the Virtual cell" *Proceedings of the Pacific Symposium on Biocomputing*, 228-239 (1999).
Schena, et al., "Quantitative monitoring of gene expression patterns with a complementary DNA microarray," *Science*, 270(5235):467-470 (1995).
Schilling, et al., "Combining Pathway Analysis with Flux Balance Analysis for the Comprehensive Study of Metabolic Systems," *Biotechnol Bioeng*, 71(4):286-306 (2000-2001).
Schilling, et al., "Genome-scale metabolic model of *Helicobacter pylori* 26695," *J Bacteriol*, 184(16):4582-4593 (2002).
Schilling, et al., "Metabolic Pathway Analysis: Basic Concepts and Scientific Applications in the Post-genomic Era," *Biotechol Prog*, 15(3):296-303 (1999).
Schilling, et al., "Theory for the Systematic Definition of Metabolic Pathways and Their Use in Interpreting Metabolic Function from a Pathway-Oriented Perspective," *J Theor Biol*, 203(3):229-248 (2000).
Schilling, et al., "Toward Metabolic Phenomics: Analysis of Genomic Data Using Flux Balances," *Biotechnol Prog*, 15(3):288-295 (1999).
Schneider, et al., "The *Escherichia coli* gabDTPC operon: specific gamma-aminobutyrate catabolism and nonspecific induction," *J Bacteriol*, 184(24):6976-6986 (2002).
Schuster, et al., "A general definition of metabolic pathways useful for systematic organization and analysis of complex metabolic networks," *Nature Biotechnol*, 18(3):326-332 (2000).
Schuster, et al., "Detection of elementary flux modes in biochemical networks: a promising tool for pathway analysis and metabolic engineering," *Trends Biotechnol*, 17(2):53-30 (1999).
Schuster, et al., "Exploring the pathway structure of metabolism: decomposition into subnetworks and application to Mycoplasma pneumoniae," *Bioinformatics*, 18(2):351-361 (2002).
Schuster, S and Hilgetag, C, "On elementary flux modes in biochemical reaction systems at steady state," *J Biol Syst*, 2(2):165-182 (1994).
Schwikowski, et al., "A network of protein-protein interactions in yeast," *Nature Biotechnol*, 18(12):1257-1261 (2000).
Scott, et al., "The Pendred Syndrome Gene Encodes a Chloride-Iodide Transport Protein," *Nat Genet*, 21(4):440-443 (1999).
Sedivy, J and Fraenkel, D, "Fructose bisphosphatase of *Saccharomyces cerevisiae*. Cloning, disruption and regulation of the FBP1 structural gene," *J Mol Biol*, 186(2):307-319 (1985).
Selkov, et al., "A reconstruction of the metabolism of *Methanococcus jannaschii* from sequence data," *Gene*, 197(1-2):GC11-26 (1997).
Selkov, et al., "Functional Analysis of Gapped Microbial Genomes: Amino Acid Metabolism of Thiobacillus Ferroxidans," *Proc Natl Acad Sci U.S.A.*, 97(7):3509-3514 (2000).
Selkov et al., "MPW: the metabolic pathways database," *Nucleic Acids Res*, 26(1):43-45 (1998).
Selkov, et al., "The metabolic pathway collection from EMP: the enzymes and metabolic pathways database," *Nucleic Acids Res*, 24(1):26-28 (1996).
Shen-Orr, et al., "Network motifs in the transcriptional regulation network of *Escherichia coli*," *Nat Genet*, 31(1):64-68 (2002).
Sherlock, et al., "The physiology of L-methionine catabolism to the secondary metabolite ethylene by *Escherichia coli*," *Curr Opin Immunol*, 12:201-205 (2000).
Shipston,, N and Bunch, AW, "The physiology of L-methionine catabolism to the secondary metabolite ethylene by *Escherichia coli*," *J Gen Microbiol*, 135(6), 1489-1497 (1989).
Silve, et al., The immunosuppressant SR 31747 blocks cell proliferation by inhibiting a steroid isomerase in *Saccharomyces cerevisiae*, *Mol Cell Biol*, 16(6):2719-2727 (1996).
Skouloubris, et al., "The *Helicobacter pylori* UreI protein is not involved in urease activity but is essential for bacterial survival in vivo," *Infect Immun*, 66(9):4517-4521 (1998).
Smith, et al., "Functional analysis of the genes of yeast chromosome V by genetic footprinting," *Science*, 274(5295):2069-2074 (1996).
Sorlie, et al., "Gene expression patterns of breast carcinomas distinguish tumor subclasses with clinical implications," *Proc Natl Acad Sci U.S.A.*, 98(19):10869-10874 (2001).
Stark, et al., "Amino acid utilisation and deamination of glutamine and asparagine by *Helicobacter pylori*,"*J Med Microbiol*, 46(9):793-800 (1997).
Stephanopoulos, "Metabolic engineering," *Curr Opin Biotechnol*, 5(2):196-200 (1994).
Stephanopoulos, G, "Metabolic Engineering," *Biotechnol Bioeng*, 58(2-3):119-120 (1998).
Summers, et al., "*Saccharomyces cerevisiae* cho2 mutants are deficient in phospholipid methylation and cross-pathway regulation of inositol synthesis" *Genetics*, 120(4):909-922 (1988).
Swartz, 3, "A PURE approach to constructive biology," *Nat Biotechnol*, 19(8):732-733 (2001).
Syvanen, A, "Accessing genetic variation: Genotyping single nucleotide polymorphisms," *Nat Rev Genet*, 2(12):930-942 (2001).
Szambelan, et al., "Use of *Zymomonas mobilis* and *Saccharomyces cerevisiae* mixed with *Kluyveromyces fragilis* for improved ethanol production from Jerusalem artichoke tubers,"*Biotechnol Lett*, 26(10):845-848 (2004).
Tamayo, et al., "Interpreting patterns of gene expression with self-organizing maps: methods and application to hematopoietic differentiation," *Proc Natl Acad Sci U.S.A.*, 96(6):2907-2912 (1999).
Tanaka, K, and Zerez, C, "Red cell enzymopathies of the glycolytic pathway," *Semin Hematol*, 27(2):165-185 (1990).
Taniguchi, M and Tanaka, T, "Clarification of interactions among microorganisms and development of co-culture system for production of useful substances," *Adv Biochem Eng Biotechnol*, 90:35-62 (2004).
Tao, et al., "Engineering a homo-ethanol pathway in *Escherichia coli*: increased glycolytic flux and levels of expression of glycolytic genes during xylose fermentation," *J Bacteriol*, 183(10):2979-2988 (2001).

ter Linde, et al., "Genome-wide transcriptional analysis of aerobic and anaerobic chemostat cultures of *Saccharomyces cerevisiae*," *J Bacteriol*, 181(24):7409-7413 (1999).

Thomas, R, "Boolean Formalization of Genetic Control Circuits," *J Theor Biol*, 42(3):563-585 (1973).

Thomas, R, "Logical Analyses of Systems Comprising Feedback Loops," *J Theor Biol*, 73(4):631-656 (1978).

Thomas, D and Surdin-Kerjan, Y, "Metabolism of sulfur amino acids in *Saccharomyces cerevisiae*," *Microbiol Mol Biol Rev*, 61(4):503-532 (1997).

Tomb, et al., "The complete genome sequence of the gastric pathogen *Helicobacter pylori*," *Nature*, 388(6642):539-547 (1997).

Tomita, et al., "E-Cell: Software Environment for Whole-Cell Simulation," *Bioinformatics*, 15(1):72-84 (1999).

Trotter, et al., "A genetic screen for aminophospholipid transport mutants identifies the phosphatidylinositol 4-kinase, STT4p, as an essential component in phosphatidylserine metabolism," *J Biol Chem*, 273(21):13189-13196 (1998).

Uetz, et al., "A comprehensive analysis of protein-protein interactions in *Saccharomyces cerevisiae*," *Nature*, 403(6770):623-627 (2000).

Van den Berg, M and Steensma, H, "ACS2, a *Saccharomyces cerevisiae* gene encoding acetyl-coenzyme A synthetase, essential for growth on glucose," *Eur J Biochem*, 231(3):704-713 (1995).

van Dijken, et al., "Alcoholic fermentation by 'non-fermentative' yeasts," *Yeast*, 2(2):123-127 (1986).

van Dijken, et al., "Kinetics of growth and sugar consumption in yeasts," *Antonie Van Leeuwenhoek*, 63(3-4):343-352 (1993).

Vanrolleghem, et al., "Validation of a Metabolic Network for *Saccharomyces cerevisiae* Using Mixed Substrate Studies," *Biotechnol Prog*, 12(4):434-448 (1996).

Varma, A and Palsson, B, "Metabolic capabilities of *Escherichia coli*. II: Optimal Growth Patterns," *J Theor Biol*, 165:503-522 (1993).

Varma, A and Palsson, B, "Metabolic capabilities of *Escherichia coli*: I. Synthesis of Biosynthetic Precursors and Cofactors," *J Theor Biol*, 165:477-502 (1993).

Varma, A and Palsson, B, "Parametric sensitivity of stoichiometric flux balance models applied to wild-type *Escherichia coli* metabolism," *Biotechnol Bioeng*, 45(1):69-79 (1995).

Varma, A and Palsson, B, "Predictions for Oxygen Supply Control to Enhance Population Stability of Engineered Production Strains," *Biotechnol Bioeng*, 43(4):275-285 (1994).

Varma, A and Palsson, B, "Stoichiometric flux balance models quantitatively predict growth and metabolic by-product secretion in wild-type *Escherichia coli* W3110," *Appl Environ Microbiol*, 60(10):3724-3731 (1994).

Varma, et al., "Metabolic Flux Balancing: Basic Concepts, Scientific and Practical Use," *Biotechnology*, 12:994-998 (1994).

Varma, et al., "Biochemical Production Capabilities of *Escherichia coli*," *Biotechnol Bioeng*, 42(1):59-79 (1993).

Varma, et al., "Stoichiometric Interpretation of *Escherichia coli* Glucose Catabolism Under Various Oxygenation Rates," *Appl Environ Microbiol*, 59(8):2465-2473 (1993).

Varner, J and Ramkrishna, D, "Mathematical Models of Metabolic Pathways," Curr Opin Biotechnol, 10(2):146-150 (1999).

Velculescu, et al., "Analysing uncharted transcriptomes with SAGE," *Trends Genet*, 16(10):423-425 (2000).

Venter, et al., "Shotgun sequencing of the human genome," *Science*, 280(5369):1540-1542 (1998).

Verduyn, C, "Physiology of yeasts in relation to biomass yields," *Antonie Van Leeuwenhoek*, 60(3-4):325-353 (1991).

Verduyn, et al., "A theoretical evaluation of growth yields of yeasts," *Antonie Van Leeuwenhoek*, 59(1):49-63 (1991).

Verduyn, et al., "Energetics of *Saccharomyces cerevisiae* in anaerobic glucose-limited chemostat cultures," *J Gen Microbiol*, 136:405-412 (1990).

Vissing, et al., "Paradoxically Enhanced Glucose Production During Exercise in Humans with Blocked Glycolysis Caused by Muscle Phosphofructokinase Deficiency," *Neurology*, 47(3):766-771 (1996).

Wang, et al., "Computer-aided baker's yeast fermentations," *Biotechnol and Bioeng*, 19(1):69-86 (1977).

Wang, et al., "Computer control of bakers' yeast production," *Biotechnol and Bioeng*, 21:975-995 (1979).

Waterston, R and Sulston, J, "The Human Genome Project: reaching the finish line," *Science*, 282(5386):53-54 (1998).

Wen et al., "Large-scale temporal gene expression mapping of central nervous system development," *Proc Natl Acad Sci U.S.A.*, 95(1):334-339 (1998).

Wiback, SJ and Palsson, B, "Extreme pathway analysis of human red blood cell metabolism," *Biophys J*, 83:808-818 (2002).

Wieczorke, et al., "Concurrent knock-out of at least 20 transporter genes is required to block uptake of hexoses in *Saccharomyces cerevisiae*," *FEBS Lett*, 464(3):123-128 (1999).

Wills, C and Melham, T, "Pyruvate carboxylase deficiency in yeast: a mutant affecting the interaction between the glyoxylate and Krebs cycles," *Arch Biochem Biophys*, 236(2):782-791 (1985).

Wingender, et al., "The TRANSFAC system on gene expression regulation," *Nucleic Acids Res*, 29(1):281-283 (2001).

Winzeler, et al., "Functional characterization of the *S. cerevisiae* genome by gene deletion and parallel analysis," *Science*, 285(5429):901-906 (1999).

Wong, P. et al., "Mathematical Model of the Lac Operon: Inducer Exclusion, Catabolite Repression, and Diauxic Growth on Glucose and Lactose," *Biotechnol Prog*,13(2):132-143 (1997).

Xie, L and Wang, D, "Energy Metabolism and ATP Balance in Animal Cell Cultivation Using a Stoichiometrically Based Reaction Network," *Biotech and Bioengineer*, 52:591-601 (1995).

Xie, L and Wang, D, "Material Balance Studies on Animal Cell Metabolism Using a Stoichiometrically Based Reaction Network," *Biotech and Bioengineer*, 52:579-590 (1996).

Xie, L. and Wang, D, "Integrated Approaches to the Design of Media and Feeding Strategies for Fed-Batch Cultures of Animal Cells," *Trends Biotechnol*, 15(3):109-113 (1997).

Yamada, et al., "Effects of common polymorphisms on the properties of recombinant human methylenetetrahydrofolate reductase," *Proc Natl Acad Sci U.S.A.*, 98(26):14853-14858 (2001).

Yeung, et al., "Reverse engineering gene networks using singular value decomposition and robust regression," *Proc Natl Acad Sci U.S.A.*, 99(9):6163-6168 (2002).

Yeung, et al., "Model-based clustering and data transformations for gene expression data," *Bioinformatics*, 17(10):977-87 (2001).

Yoshida, et al., "Combined transcriptome and proteome analysis as a powerful approach to study genes under glucose repression in *Bacillus subtilis*," *Nucleic Acids Res*, 29(3):683-692 (2001).

Zanella, A and Bianchi, P, "Red cell pyruvate kinase deficiency: from genetics to clinical manifestations," *Bailliere's Best Pract Res Clin Haematol* 13(1):57-81 (2000).

Zeng, et al., "Use of respiratory quotient as a control parameter for optimum oxygen supply and scale-up of 2,3-butanediol production under microaerobic conditions," *Biotechnol Bioeng*, 44(9):1107-1114 (1994).

Zhu, J and Zhang, M, "SCPD: a promoter database of the yeast *Saccharomyces cerevisiae*," *Bioinformatics*, 15(7-8):607-611 (1999).

Zigova, "Effect of R and pre-seed conditions of biomass and galactosyl transferase production during fed-batch culture of *S. cerevisiae* BT150," *J Biotechnol*, 80(1):55-62 (2000).

Zweytick, et al., "Biochemical characterization and subcellular localization of the sterol C-24(28) reductase, erg4p, from the yeast *Saccharomyces cerevisiae*," *FEBS Lett*, 470(1):83-87 (2000).

URL Genome.jp Website, KEGG *Bacillus subtillis*, 1-7 (2005).

URL mips.gsf.de/proj/yeast/pathways/ on Jun. 6, 2008, MIPS, website: Comprehensive Yeast Genome Database—Pathways (1998).

www.1-sis.org.uk/WITBRL.php; Hoppert, Michael 2008.

Duarte, et al., "Reconstruction and validation of *Saccharomyces cerevisiae* iND750, a fully compartmentalized genome-scale metabolic model," *Genome Res* 14(7): 1298-1309 (2004).

Feist and Palsson "The growing scope of applications of genome-scale metabolic reconstructions using *Escherichia coli*," *Natural Biotech* 26(6):659-667 (2008).

Fotheringham, "Engineering biosynthetic pathways: new routes to chiral amino acids," *Curr Opin in Chem Biology* 4(1): 120-124 (2000).

Gombert and Nielsen, "Mathematical modeling of metabolism," *Curr Opin in Biotech* 11(2): 180-186 (2000).

Guardia, et al., "Cybernetic modeling and regulation of metabolic pathways in multiple steady states of hybridoma cells." *Biotech Progress* 16(5):847-853 (2000).

Kaufman, et al., "Towards a logical analysis of the immune response." *J of Theoretical Biology* 114(4):527-561 (1985).

Kunst and Devine, "The project of sequencing the entire *Bacillus substilis* genome," *Res in Microbiology* 142:905-912 (1991).

Lee, et al., "Incorporating qualitative knowledge in enzyme kinetic models using fuzzy logic." Biotech and Bioengineer 62(6):722-729 (1999).

Lynd, et al., "Biocommodity Engineering," *Biotechnology Progress* 15:777-793 (1999).

McAdams and Shapiro, "Circuit simulation of genetic networks," *Science* 269:651-656 (1995).

McAdams and Arkin, "Stochastic mechanisms in gene expression," *Proc of the National Academy of Sciences of the USA* 94(3):814-819 (1997).

McAdams and Arkin, "It's a noisy business! Genetic regulation at the nanomolar scale." *Trends in Genetics* 15(2):65-69 (1999).

Ostergaard, et al., "Increasing galactose consumption by *Saccharomyces cerevisiae* through metabolic engineering of the GAL gene regulatory network," *Nat Biotech* 18:1283-1286(2000).

Pieper and Reineke, "Engineering bacteria for bioremediation," *Curr Opin in Biotech*II(3):262-270(2000).

Raclot, et al., "Selective release of human adipocyte fatty acids according to molecular structure," *Biochem J* 324 (Pt3):911-915 (1997).

Rao and Arkin, "Control motifs for intracellular regulatory networks," *Annual Rev of Biomed Engineer* 3:391-419 (2001).

Savageau, "Development of fractal kinetic theory for enzyme-catalysed reactions and implications for the design of biochemical pathways," *Biosystems* 47(I-2):9-36 (1998).

Savinell and Palsson, "Network Analysis of Intermediary Metabolism using Linear Optimization. II. Interpretation of Hybridoma Cell Metabolism," *J Theor Biol* 154:455-473(1992).

Savinell and Palsson, "Network Analysis of Intermediary Metabolism using Linear Optimization. I. Development of Mathematical Formalism," *J Theor Biol*. 154:421-454 (1992).

Somogyi and Sniegoski "Modeling the complexity of genetic networks: understanding the mucigenic and pleitropic regulation," *Complexity* I(6):45-63 (1996).

Tandeitnik, et al., "Modeling of biological neurons by artificial neural networks," *Nineteenth Convention of Electrical and Electronics Engineers in Israel*. Jerusalem, Israel. New York. NY USA, pp. 239-242 (1996).

Thieffry and Thomas, "Dynamical behavior of biological regulatory networks II. Immunity control in bacteriophage lambda." *Bulletin of Math Biology* 57(2):277-297 (1995).

Varner, "Large-scale prediction of phenotype: concept," *Biotech and Bioengineer* 69(6): 664-678 (2000).

Vaseghi, et al., "In vivo Dynamics of the pentose phosphate pathway in *Saccharomyces cerevisiae*," *Metabolic Engineer* 1:128-140 (1999).

Vo, et al., "Reconstruction and functional characterization of the human mitochondrial metabolic network abased on proteomic and biochemical dataz," *J Biol Chem* 279(38):39532-39540 (2004).

URL affymetrix.com, Affymetrix protocol for *E. coli* Antisense Genome. (As printed Sep. 18, 2009).

URL affymetrix.com/products/arrays/specific/ecoli antisense.affx. (As printed Sep. 18, 2009).

URL asap.ahabs.wisc.edu/annotation/php/logon.php, The ASAP website. (As printed Sep. 17, 2009).

URL ca.expasy.org/sprot/, protein database SWISS—PROT. (As printed Jun. 15, 2009).

URL chem.qmw.ac.uk/iubmb/enzyme/, Enzyme Nomenclature database maintained by G.P. Moss of Queen Mary and Westfield College in the United Kingdom. (As Printed Sep. 18, 2009).

URL hsph.harvard.edu. dChipSoftware:Analysis and visualization of gene expression and SNP microarrays. (As printed Jun. 15, 2009).

URL Dictionary.com pp. 1-2, Matrix (As printed Nov. 1, 2004).

URL ecocyc.panbio.com/ecocyc/ecocyc.html, EcoCyc. (As printed Sep. 18, 2009).

URL enzobio.com/lifesci_index.htm, Enzo BioArray Terminal Labeling Kit protocol. (As printed Sep. 18, 2009).

URL genetics.wisc.edu/, *E. coli* Genome Project at the University of Wisconsin. (As printed Sep. 18, 2009).

URL genome.ad.jp/kegg/, Kyoto Encyclopedia of Genes and Genomes database (KEGG). (As printed Sep. 18, 2009).

URL Genome.jp Website, KEGG *Bacillus subtillis*, 1-7. (As printed Jun. 1, 2005).

URL genome.tugraz.at/Software/Genesis/Description.html, "Genesis" software. (As printed Sep. 18, 2009).

URL igweb.integratedgenomics.com/MPW/, Metabolic pathways database (MPW). (As printed Sep. 18, 2009).

URL integratedgenomics.com, ERGO from Integrated Genomics. (As printed Sep. 18, 2009).

URL mips.gsf.de/proj/yeast/pathways/ on Jun. 6, 2008, MIPS, website: Comprehensive Yeast Genome Database—Pathways (1998). (As printed Sep. 18, 2009).

URL ncbi.nlm.gov, Genbank genome database.(As printed Jun. 15, 2009).

URL ncbi.nlm.nih.gov/entrez/query.fcgi?db=Genome, The NCBI Entrez Genome database. (As printed Jun. 1, 2009).

URL ncbi.nlm.nih.gov/LocusLink/, LocusLink database maintained by the NCBI. (As printed Sep. 18, 2009).

URL ncbi.nlm.nih.gov/Taxonomy/taxonomyhome.html/. (As printed Sep. 18, 2009).

URL nslij-genetics.org/search_omim.html, Online Mendelian Inheritance in Man database, Center for Medical Genetics, Johns Hopkins University (Baltimore, MD) and National Center for Biotechnology Information, National Library of Medicine (Bethesda, MD). (As printed Sep. 18, 2009).

URL qiagen.com, Qiagen RNeasy Mini Kit. (As printed Sep. 18, 2009).

URL rana.lbl.gov/EisenSoftware.htm, "Cluster" software. (As printed Sep. 18, 2009).

URL genome-www.stanford.edu/~sherlock/cluster.html, "XCluster" software. (As printed Sep. 18, 2009).

URL systembiology.ucsd.edu. (As printed Sep. 18, 2009).

URL tigr.org, The Institute for Genome Research, J Craig Venter Institute. (As printed Sep. 18, 2009).

URL tula.cifn.unam.mx:8850/regulondb/regulon_intro.frameset. (As printed Sep. 18, 2009).

URL workbench.sdsc.edu/, Biology Workbench. (As printed Sep. 18, 2009).

URL 216.190.101.28/IGwit/ or wit.mcs.anl.gov/WIT/, What is There (WIT). (As printed Sep. 18, 2009).

www.1-sis.org.uk/WITBRL.php; Hoppert, Michael 2004. (As printed Nov. 23, 1008).

METHOD FOR THE EVOLUTIONARY DESIGN OF BIOCHEMICAL REACTION NETWORKS

CROSS REFERENCE TO RELATED APPLICATIONS

This application is a continuation application of U.S. application Ser. No. 09/940,686, filed Aug. 27, 2001, now U.S. Pat. No. 7,127,379; which claims the benefit under 35 USC §119 (e) to U.S. Application Ser. No. 60/265,554 filed Jan. 31, 2001. The disclosure of each of the prior applications is considered part of and is incorporated by reference in the disclosure of this application.

BACKGROUND OF THE INVENTION

1. Field of the Invention

The invention relates generally to biochemical reaction networks and more specifically to reconstruction of metabolic networks in an organism to obtain optimal desired whole cell properties.

2. Background Information

Genome sequencing and annotation technologies are giving us detailed lists of the molecular components that cells are comprised of, and high-throughput technologies are yielding information about how these components are used. Thus we are approaching the stage where biological design is possible on a genome scale. It has proven difficult to 'splice' one gene from one organism into another and produce predictable results. The primary reason is that every component in a living cell has been honed through a lengthy evolutionary process to 'fit' optimally into the overall function of the cell. Simply introducing a foreign gene, or deleting an existing gene does not lead to predictable nor optimal results. Methods are needed to a priori predict the consequences of single or multiple gene deletions or additions on the function of an entire cellular function and force the remaining components to function in a predetermined manner. Such methods are lacking, although limited progress has been made with metabolic function on a cellular scale.

The interest in the redirection of metabolic fluxes for medical and industrial purposes has existed for some time. As a result of this interest, the field of metabolic engineering has been born, and the primary goal of metabolic engineering is to implement desirable metabolic behavior in living cells. Advances and applications of several scientific disciplines including computer technology, genetics, and systems science lie at the heart of metabolic engineering.

The traditional engineering approach to analysis and design utilizes a mathematical or computer model. For metabolism this would require a computer model that is based on fundamental physicochemical laws and principles. The metabolic engineer then hopes that such models can be used to systematically 'design' a new and improved living cell. The methods of recombinant DNA technology should then be applied to achieve the desired cellular designs.

The 25-30 year history of metabolic analysis has demonstrated the need to quantitate systemic aspects of cellular metabolism, (see e.g., Fell D., Understanding the control of metabolism, (London, Portland Press) (1996); Heinrich R., et al., Metabolic regulation and mathematical models, *Progress in Biophysics and Molecular Biology*, 32:1-82, (1977); Heinrich R. and Schuster S., The regulation of cellular systems, (New York, Chapman & Hall), xix, p. 372 (1996); Savageau M. A., Biochemical systems analysis. I. Some mathematical properties of the rate law for the ecomponent enzymatic reactions, *J. Theor. Biol.* 25(3):365-69 (1969)). There are significant incentives to study metabolic dynamics. A quantitative description of metabolism and the ability to produce metabolic change is not only important to achieve specific therapeutic goals but has general importance to our understanding of cell biology. Important applications include strain design for the production of therapeutics and other biochemicals, assessment of the metabolic consequences of genetic defects, the synthesis of systematic methods to combat infectious disease, and so forth. Quantitative and systemic analysis of metabolism is thus of fundamental importance. However, a review in the field has concluded that "despite the recent surge of interest in metabolic engineering, a great disparity still exists between the power of available molecular biological techniques and the ability to rationally analyze biochemical networks" (Stephanopoulos G., Metabolic engineering. *Current Opinions in Biotechnology*, 5:196-200 (1994)). Although this statement is a few years old, it still basically holds true. This conclusion is not surprising for we are competing with millions of years of natural evolution that achieves the best fitness of an organism in a given environment.

Although partial gene regulatory networks containing a small number of reactions have been designed (reviewed in Hasty et al., Computational studies of gene regulatory networks: In numero molecular biology, *Nature*, 2: 268-79 (2001)), the a priori design of biochemical regulatory networks, such as metabolic networks with defined performance characteristics and their subsequent construction has not been reduced to practice. The primary reason is that reliable detailed kinetic models cannot be constructed for an entire metabolic network, mainly because there are too many kinetic parameters whose numerical values must be determined and the detailed kinetic equations are by-and-large unknown. Thus, a priori design of optimal biochemical reaction networks, such as metabolism, is not possible because predictive kinetic models cannot be achieved. In fact, the values of the kinetic constants change with time due to mutations and an evolutionary process.

Heretofore it has been impossible to predict the end point of evolutionary processes as they are expected to be the outcome of the selection from random events. This invention discloses a method that allows for the a priori calculation of the endpoint of the evolution of metabolic networks in a defined environment. Although there are other mathematical modeling methods that are based on optimization principles in biological systems; i.e. the cybernetic modeling approach (Varner J. and Ramkrishna D., "Mathematical models of metabolic pathways," *Curr. Opin. Biotechnol.*, 10(2):146-50, (1999), they are not amenable to the design of biological networks due to the number of parameters required. It thus gives the basis for the use of an evolutionary process to create or build such designs.

SUMMARY OF THE INVENTION

The present invention relates to a method for achieving an optimal function of a biochemical reaction network in a living cell. The biochemical reaction network can be a comprehensive biochemical reaction network, a substantially whole biochemical reaction network, or a whole biochemical reaction network. The method can be performed in silico using a reconstruction of a biochemical reaction network of a cell. The method can further include laboratory culturing steps to confirm and possibly expand the determinations made using the in silico steps, and to produce a cultured cell, or population of cells, with optimal functions.

The method can be performed by representing a listing of biochemical reactions in a network in a computer, such as by providing a database of biochemical reactions in a network; using optimization methods to calculate the optimal properties of the network; altering the list of reactions in the network and re-computing the optimal properties; and repeating the process described above until the desired performance is reached. The method may further include constructing the genetic makeup of a cell to contain the biochemical reactions which result from the optimization procedure; placing the cells constructed thereunder in culture under the specified environment; and cultivating the cells for a sufficient period of time under conditions to allow the cells to evolve to the determined desired performance.

The biochemical reaction network can be a metabolic network, for example a regulatory network. In addition, the cell whose genetic makeup is constructed can be a prokaryotic cell or a eukaryotic cell; such as *E. coli*, *S. cerevisiae*, chinese hamster ovary cells, and the like. Furthermore, the genetic makeup of a cell can be constructed by altering one or more genes in the cell, for example by addition or deletion, or by altering the regulation of a gene through its regulatory components (e.g., promoter, transcription factor binding sites, etc.). In another aspect, the invention provides an enriched population of cells produced by the method described above.

In another aspect, the present invention provides a method for achieving optimal functions of a comprehensive biochemical reaction network in a cell by providing a database including biochemical reactions in the network; using optimization methods to calculate the optimal properties of the network; receiving a user's selection for altering the reactions in the network and recomputing the optimal properties; repeating optimization until the desired property criterion is met; displaying the results of the optimization for constructing the genetic makeup of a cell so that it contains the biochemical reactions as a result of the optimization information; culturing the cells constructed under the specified environment conditions; and cultivating the cells for a sufficient period of time so that the cells evolve to the desired performance.

The optimization method may be carried out using a computer system provided by the present invention. The computer system typically includes a database that provides information regarding one or more biochemical reaction networks of at least one organism; a user interface capable of receiving a selection of one or more biochemical reaction networks for optimization and/or comparison, and capable of receiving a selection of a desired performance; and a function for carrying out the optimization method calculations and recalculations. The computer system of the present invention can include a function for performing biochemical reaction network reconstruction. The database can be an internal database or an external database.

In another aspect the present invention provides a computer program product that includes a computer-usable medium having computer-readable program code embodied thereon. The program code is capable of interacting with the database and effects the following steps within the computing system: providing an interface for receiving a selection of a desired performance of the networks; determining the desired optimal properties, displaying the results of the determination, and altering the biochemical reaction network, before recalculating optimal properties of the biochemical reaction network, and repeating the process until a desired optimal function is achieved. Altering the biochemical reaction network can be performed based on an alteration manually input by a user, or can be performed automatically by the program code. The computer program can further provide an identification of database entries that are part of a reconstructed biochemical network, or can perform biochemical reaction network reconstruction.

DETAILED DESCRIPTION OF THE INVENTION

Figure 1:
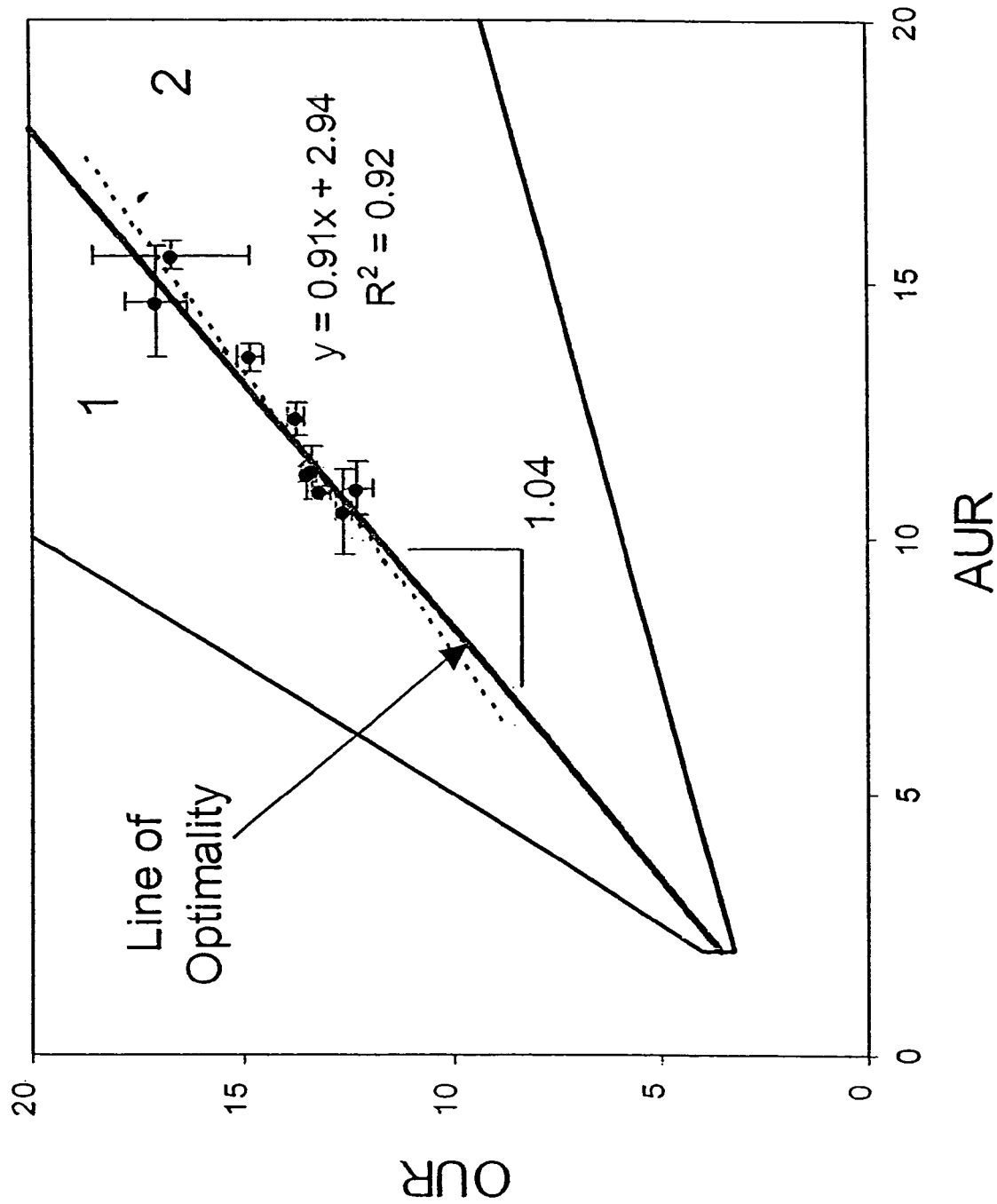
FIG. 1: The acetate uptake rate (AUR in units of mmole/g-DW/hr, g-DW is gram dry weight) versus oxygen uptake rate (OUR, in units of mmole/g-DW/hr) phenotype phase plane. The in silico defined line of optimality (LO) is indicated in the figure. The slope of this line is also indicated in the figure. The experimental data points are displayed on the figure. The error bars represent a single standard deviation, and the error bars are displayed for both the acetate and the oxygen uptake rate measurements. A linear regression was performed on the data points to define the experimentally reconstructed line of optimality. The correlation coefficient $R^2$ value for the curve fit is 0.92. Regions 1 & 2 represent distinct non-optimal metabolic phenotypes

One aspect of this invention provides a method to design the properties of a large biochemical reaction network. Using a method of this aspect of the present invention, a biochemical reaction network can be designed to a predetermined performance in a specified environment. One aspect of the invention includes:

1) using a computer reconstruction of the reaction structure of a biochemical reaction network, 2) using optimization methods to determine the optimal functionalities of the reaction network, 3) changing the reaction structure in the computer representation of the network by removing or adding a single or a multitude of genes and recalculating the optimal properties, 4) using genetic manipulations to get the gene complement in an organism to correspond to the structure of the reaction network whose optimal properties have been determined through computer simulation, and 5) using extended cultivation under a defined selection pressure to evolve the function of the actual reaction network toward the optimal solution that was predicted by the computer simulation. The adaptive evolutionary process will itself determine the best set of kinetic parameters to achieve the optimal design. More than one similar set of parameter values can be determined thorough the evolutionary process.

Using the methods and procedures disclosed herein, a biochemical reaction network can be designed a priori in a computer. Following the design of the reaction network, an evolutionary process is carried out in the laboratory under the appropriate conditions on a genetically modified organism or a wild-type strain that corresponds to the network used for the computer simulations. Organisms may achieve the optimal behavior in a non-unique fashion—that is there may be equivalent optimal solutions. Thus the invention involves a non-obvious and non-existing combination of computer design methods, genetic alteration, and evolutionary process to achieve optimal performance of biochemical reaction networks within the environment of a living cell.

In another aspect, the present invention relates to a method for determining optimal functions of a comprehensive biochemical reaction network in a living cell. The method is used to achieve a desired performance of the living cell. The method can be performed by representing a listing of the biochemical reactions in the network in a computer; using optimization methods to calculate the optimal properties of the network; altering the list of reactions in the network and re-computing the optimal properties; and repeating the altering step until the desired performance is met.

In addition to the above steps which are performed in silico, the method can further include steps involving culturing a living cell, or a population of cells. These steps include constructing the genetic makeup of a cell to contain the biochemical reactions which result from repeating the altering step until the desired performance are met; placing the cell constructed thereunder in culture under the specified environment; and cultivating the cell for a sufficient period of time and under conditions to allow the cell to evolve to the determined desired performance.

A biochemical reaction network is an interrelated series of biochemical reactions that are part of a biochemical pathway or linked biochemical pathways. Many biochemical reaction networks have been identified such as metabolic reaction networks, catabolic reaction networks, polypeptide and nucleic acid synthesis reaction networks, amino acid synthesis networks, energy metabolism and so forth. Other types of biochemical reaction networks include regulatory networks including cell signaling networks, cell cycle networks, genetic networks involved in regulation of gene expression, such as operon regulatory networks, and actin polymerization networks that generate portions of the cytoskeleton. Most of the major cell functions rely on a network of interactive biochemical reactions.

To practice the present invention, the reaction structure of a comprehensive, preferably substantially whole, or most preferably whole biochemical reaction network in an organism to be biochemically designed must be reconstructed for computer simulations. A whole biochemical reaction network includes all of the biochemical reactions of a cell related to a certain biochemical function. For example a whole metabolic reaction network includes essentially all of the biochemical reactions that provide the metabolism of a cell. Metabolic reaction networks exemplify a universal biochemical reaction network found in some form in all living cells.

A comprehensive biochemical reaction network is an interrelated group of biochemical reactions that effect a detectable property, and that can be modified in a predictable manner with respect to the effect of such modifications on the detectable property in the context of a living cell. For example, a comprehensive biochemical reaction network can include core reactions that effect the yield of a biomolecule produced by the cell, even though the core reactions include only a portion of the reactions in the whole biochemical reaction network involved in yield of the biomolecule, provided that computational methods can be used to predict the effect of changes in the core biochemical reactions on the yield in a living cell.

A substantially whole biochemical reaction network is an interrelated group of biochemical reactions that are responsible for a detectable property of a living cell. Substantially whole biochemical reaction networks include core reactions as well as secondary reactions that have an effect on the detectable property, even though this effect can be relatively minor. Changes in substantially whole biochemical reaction networks can be predicted using computational methods. The present invention can also utilize the majority of reactions in a whole biochemical reaction network, rather than a comprehensive, substantially whole, or whole biochemical reaction network.

Optimal properties, also referred to herein as optimal functions, determined using the methods of the current invention include, for example, glycerol uptake rate, oxygen uptake rate, growth rate, sporulation occurrence and/or rates, rates of scouring of rare elements under nutritionally poor conditions, biomass, and yields of biomolecules such as proteins, carbohydrates, antibiotics, vitamins, amino acids, fermentation products, such as lactate production. Optimal properties also include, for example, yields of chiral compounds and other low molecular weight compounds. Optimal properties also include, for example, the maximal internal yields of key cofactors, such as energy carrying ATP or redox carrying NADPH and NADH. Optimal properties can also be defined by a cellular engineer to include properties such as flux rates through key reactions in the biochemical reaction network. The current invention allows an optimal performance related to one or more of these properties to be achieved. For example, the methods allow a specific desired growth rate or specific desired yield to be achieved.

Typically for the methods of the current invention, the biochemical reactions of a reconstructed biochemical reaction network are represented in a computer. This representation can include a listing of the biochemical reactions in the reconstructed biochemical reaction network. The listing can be represented in a computer database, for example as a series of tables of a relational database, so that it can be interfaced with computer algorithms that represent network simulation and calculation of optimality properties.

The biochemical network reconstruction must be of high quality for the present invention. The process of high quality biochemical reaction network, specifically metabolic reaction network, reconstruction has been established M. W. Covert, C. H. Schilling, I. Famili, J. S. Edwards, I. I. Goryanin, E. Selkov, and B. O. Palsson, "Metabolic modeling of microbial stains in silico," *Trends in Biochemical Sciences*, 26: 179-186 (2001); Edwards J., and Palsson, B, Metabolic flux balance analysis and the in silico analysis of *Escherichia coli* K-12 gene deletions, *BMC Structural Biology*, 1(2) (2000a); Edwards J. S., and Palsson, B, O., Systemic properties of the *Haemophilus influenzae* Rd metabolic genotype, *Journal of Biological Chemistry*, 274(25): 17410-16, (1999); Karp P. D. et al., HinCyc: A knowledge base of the complete genome and metabolic pathways of *H. influenzae*, ISMB 4:116-24, (1996); Karp P. D. et al., The EcoCyc and MetaCyc databases, *Nucleic. Acids Res.* 28(1):56-59 (2000); Ogata et al., KEGG: Kyoto encyclopedia of genes and genomes, *Nucleic Acids Res.* 27(1):29-34 (1999); Schilling C. H. and Palsson B. O., Assessment of the metabolic capabilities of *Haemophilus influenzae* Rd through a genome-scale pathway analysis, *J. Theor. Biol.*, 203(3): 249-83 (2000); Selkov E. Jr. et al., MPW: the metabolic pathways database, *Nucleic Acids Res.*, 26(1): 43-45 (1998); Selkov E. et al., A reconstruction of the metabolism of *Methanococcus jannaschii* from sequence data. *Gene* 197(1-2):GC11-26 (1997)). This process involves the use of annotated genome sequences, and biochemical and physiological data. These annotated genome sequences and biochemical and physiological data can be found in one or more internal or external databases, such as those described in detail in the discussion of the computer systems of the current invention below. Careful analysis of the reconstructed network is needed to reconcile all the data sources used. Similar methods can be used for the reconstruction of other biochemical reaction networks.

A method of this aspect of the present invention then uses the reconstructed comprehensive, substantially whole, or whole biochemical reaction network to determine optimal properties of the comprehensive, substantially whole, or whole biochemical reaction network under specified and varying environmental conditions. This determination allows the design of a biochemical reaction network that achieves a desired performance in a specified environment. This in turn, can be combined with steps for constructing the genetic makeup of a cell and cultivating the cell, described below, to provide a method for developing a recombinant cell, or a population of cells, that achieves the desired performance.

Optimal properties of the comprehensive, substantially whole, or whole biochemical reaction network under a series of specified environments can be determined using computational methods known as optimization methods. Optimization methods are known in the art (see e.g., Edwards and Palsson (1999)). The optimization methods used in the methods of the current invention can, for example and not intended to be limiting, utilize a combination of flux balance analysis (FBA), phase plane analysis (PhPP), and a determination of a Line of Optimality (LO), as described in further detail below.

The reconstructed metabolic network can then be used to perform quantitative simulations of the metabolic flux distribution in a steady state using established methods (Bonarius et al., Flux analysis of underdetermined metabolic networks: The quest for the missing constraints, *Trends in Biotechnology*, 15(8): 308-14 (1997); Edwards J. S., et al., Metabolic flux Balance Analysis, In: (Lee S. Y., Papoutsakis E. T., eds.) Metabolic Engineering: Marcel Deker. P 13-57 (1999); Varma A. and Palsson B. 0, Metabolic flux balancing: Basic concepts, Scientific and practical use, *Bio/Technology*

12:994-98 (1994a)). Computer simulations of the metabolic network can be performed under any conditions. Furthermore, any reaction list can be simulated in a computer by changing the parameters describing the environment and the contents of the reaction list.

The metabolic capabilities of a reconstructed metabolic network can be assessed using the established method of flux balance analysis (FBA) (Bonarius et al., (1997); Edwards et al. (1999); Varma and Palsson (1994a)). FBA is based on the conservation of mass in the metabolic network in a steady state and capacity constraints (maximal fluxes through the reactions) on individual reactions in the network. Additionally, experimentally determined strain specific parameters are also required, the biomass composition (Pramanik J. and Keasling J. D., Stoichiometric model of *Escherichia coli* metabolism: Incorporation of growth-rate dependent biomass composition and mechanistic energy requirements, *Biotechnology and Bioengineering*, 56(4): 398-421 (1997)) and the maintenance requirements (Varma A. and Palsson B. O., Stoichiometric flux balance models quantitatively predict growth and metabolic by-product secretion in wild-type *Escherichia coli* W3110. *Applied and Environmental Microbiology*, 60(10): 3724-31 (1994b)). These factors are then used to calculate the flux distribution through the reconstructed metabolic network.

More specifically, the definition of these factors leads mathematically to a closed solution space to the equations in which all feasible solutions lie. There are thus many possible solutions (flux distributions) to the problem. The 'best' or optimal solution within the set of all allowable solutions can then be determined using optimization procedures and a stated objective. The optimization procedure used has been linear programming and the objective is the optimal use of the biochemical reaction network to produce all biomass components simultaneously. These optimization procedures are established and have been published (Varma and Palsson (1994a); Bonarious (1997); and Edwards et al. (1999)). The comparison of the calculated behavior based on the optimal growth objective to the experimental data is favorable in the majority of cases (Varma (1994b); Edwards J. S., Ibarra R. U., and Palsson B. O. (herein incorporated by reference), In silico predictions of *Escherichia coli* metabolic capabilities are consistent with experimental data, *Nat Biotechnol.*, 19(2): 125-30 (2001a); and Edwards, Ramakrishna, and Palsson, Characterizing phenotypic plasticity: A phenotype phase plane analysis, *Biotech Bioeng*, In Press, (2001b)). In other words, these solution confinement and optimization procedures lead to a prediction of the optimal uses of a biochemical reaction network to support cellular growth and for pre-evolved strains give a good estimate of actual biological function.

The use of alternate survival objectives, such as sporulation, and scouring of rare elements under nutritionally poor conditions, has not been described. Competition and evolution under these conditions can also be used to define and generate optimal network functions.

These procedures lead to the calculation of optimal function under a single growth condition. This is very limiting and a method to analyze a large number of growth conditions is needed.

As stated above, all steady state metabolic flux distributions are mathematically confined to the solution space defined for a given reconstructed metabolic network, where each solution in the solution space corresponds to a particular flux distribution through the network or a particular metabolic phenotype (Edwards and Palsson (1999)). Under a single specified growth condition, the optimal metabolic flux distribution in the cone can be determined using linear programming (LP) or other related approaches for calculating optimal solutions of such problems. If the constraints vary, the shape of the cone changes and the optimal flux vector may qualitatively change. Phenotype Phase Plane (PhPP) analysis considers all possible variations in two or more constraining environmental variables. This method is now disclosed.

Uptake rates of two nutrients (such as the carbon substrate and oxygen) can be defined as two axes on an (x,y)-plane, and the optimal flux distribution can be calculated for all points in this plane using the procedures described above. When this procedure is implemented for a reconstructed metabolic network that is biologically realistic, we find that there are a finite number of qualitatively different optimal metabolic flux maps, or metabolic phenotypes, present in such a plane. The demarcations on the phase plane can be defined by using shadow prices of linear optimization (Chvatal V., Linear Programming, (New York: W.H. Freeman and Co.) (1983)). The procedure described leads to the definition of distinct regions, or "phases", in the (x,y)-plane, for which the optimal use of the metabolic network is qualitatively different. Each phase can be designated as $Pn_{x,y}$, where P represents a particular phenotype or flux distribution, n is the number arbitrarily assigned to the demarcated region for this phenotype, and the two uptake rates form the axis of the plane.

The phase planes can be constructed by calculating the shadow prices throughout the two-parameter space, and lines are drawn to demarcate regions of constant shadow prices. The shadow prices define the intrinsic value of each metabolite toward the objective function (Chvatal (1983)). The shadow prices are either negative, zero, or positive, depending on the value of the metabolite to optimizing growth under a given environmental condition, as represented by particular numerical values of the uptake rates represented by the x and y axes. When shadow prices become zero as the values of the uptake rates are changed there is a qualitative shift in the optimal metabolic map. This criterion defines the lines in the PhPP.

The line of optimality (LO) is defined as the line representing the optimal relation between the two uptake fluxes corresponding to the axes of the PhPP. For aerobics, this line can be interpreted as the optimal oxygen uptake for the complete oxidation of the substrate in order to support the maximal biomass yield.

The metabolic reconstruction and phenotype phase plane analysis procedures are then used to predict the conditions under which the desired metabolic behavior, for example maximum uptake rates, will be optimal. In other words, metabolic reconstruction and PhPP are used to determine optimal performance. The maximal uptake rates lead to the definition of a finite rectangular region in the phase plane. The optimal growth condition within this rectangle will then be the predicted outcome of an evolutionary process within the given constraints.

Using the optimization procedure, the properties of the corresponding actual biochemical reaction network may not be optimal or the same as desired from a practical standpoint. The simulated reconstructed network and its synthesis in an organism may not display the optimal solution desired, also referred to herein as the desired optimal performance or desired optimal function. Lack of optimality may be due to the fact that:

1. The natural organism with an intact network has never experienced the environmental conditions of interest and never undergone growth competition and selection in this environment, or 2. The man made network is perturbed from its evolutionarily determined optimal state by genetic manipulations, through the deletion/addition of a new reaction from/to the network.

The in silico methods of the current invention are designed to resolve this second cause of lack of optimality, by altering the reactions in the network until a desired performance is achieved. Then culturing methods, which can be included in the method of the current invention as described in further detail below, can be used to resolve the first cause of the lack of optimality related to growth competition and selection.

As mentioned above, after calculation of the optimal properties, a metabolic engineer can alter the reaction list in the network, or an algorithm can be developed that automatically alters one or more reactions in the reaction list, to achieve a desired performance. After alteration of the biochemical list, optimal properties of this network under given environmental conditions can be calculated. This is an iterative design procedure that may require many different versions of the reaction list until the desired performance is achieved. The desired performance is a qualitative characteristic or quantitative value for a property calculated using an optimization procedure. Many properties for which a desired performance can be achieved are known in the art. For example, a desired performance can be a desired growth rate or a desired yield of a biomolecule such as an enzyme or an antibiotic.

The optimization method may be carried out using a computer system provided by the present invention. The computer system typically includes a database that provides information regarding one or more biochemical reaction networks of at least one organism; a user interface capable of receiving a selection of one or more biochemical reaction networks for optimization and/or comparison, and capable of receiving a selection of a desired performance; and a function for carrying out the optimization method calculations and recalculations. Furthermore, the computer system of the present invention may include a function for performing biochemical reaction network reconstruction described hereinabove.

The computer system can be a stand-alone computer or a conventional network system including a client/server environment and one or more database servers. A number of conventional network systems, including a local area network (LAN) or a wide area network (WAN), are known in the art. Additionally, client/server environments, database servers, and networks are well documented in the technical, trade, and patent literature. For example, the database server can run on an operating system such as UNIX, running a relational database management system, a World Wide Web application, and a World Wide Web Server.

Typically, the database of the computer system of the present invention includes information regarding biochemical reactions in a comprehensive biochemical reaction network, a substantially whole biochemical reaction network, or a whole biochemical reaction network. This information can include identification of biomolecular reactants, products, cofactors, enzymes, rates of reactions coenzymes, etc. involved in at least some of the biochemical reactions of the network. This information can include the stoichiometric coefficients that indicate the number of molecules of a compound that participates in a particular biochemical reaction. This information can include any and all isozymes that are found in the organism. This information can include all the related biochemical reactions that can be catalyzed by a single enzyme. This information can include the formation of oligomeric enzyme complexes, that is when many different protein molecules must non-covalently associate to form a complex that can carry out the chemical reactions. This information can include the location of the enzyme that carries out the reaction, (i.e. if it is in a membrane, in the cytoplasm, or inside an organelle such as the mitochondria). The information can also include experimentally derived or calculated rates of reactions under various conditions, biomass compositions, and maintenance requirements. This information can include non-mechanistic growth and non-growth associated maintenance requirements. This information can include mechanistic maintenance information such as inefficiency in protein synthesis. This information can include data derived from genome-scale mRNA or protein expression profiles. This information can include data on operon or regulatory structures that are associated with the expression of a particular gene. This information can include sequence variations that reflect changes in enzyme properties. This information can include a condition-dependent inclusion of a biochemical reaction, depending for instance if a gene is not expressed under the conditions of interest. Where the biochemical reaction network is a metabolic reaction network, the information for example can include known consumption rates, by-product production rates, and uptake rates.

The information in the database may include biomolecular sequence information regarding biomolecules involved in the biochemical reactions of the biochemical reaction network, for example information regarding multiple biomolecular sequences such as genomic sequences. At least some of the genomic sequences can represent open reading frames located along one or more contiguous sequences on each of the genomes of the one or more organisms. The information regarding biochemical reaction networks can include information identifying those biochemical reaction networks to which a biomolecular sequence plays a role and the specific reactions in the biochemical reaction network involving the biomolecule.

The database can include any type of biological sequence information that pertains to biochemical reactions. For example, the database can be a nucleic acid sequence database, including ESTs and/or more preferably full-length sequences, or an amino acid sequence database. The database preferably provides information about a comprehensive, substantially whole, or whole biochemical reaction network. For example, the database can provide information regarding a whole metabolic reaction network. The database can provide nucleic acid and/or amino acid sequences of an entire genome of an organism.

The database can include biochemical and sequence information from any living organism and can be divided into two parts, one for storing sequences and the other for storing information regarding the sequences. For example, the database can provide biochemical reaction information and sequence information for animals (e.g., human, primate, rodent, amphibian, insect, etc), plants, or microbes. The database is preferably annotated, such as with information regarding the function, especially the biochemical function, of the biomolecules of the database. The annotations can include information obtained from published reports studying the biochemistry of the biomolecules of the database, such as specific reactions to which a biomolecule is involved, whether the biomolecule is or encodes an enzyme, whether the sequence is a wild-type sequence, etc.

The annotations and sequences of the database provide sufficient information for a selected biochemical genotype of an organism to be identified. A biochemical genotype is a grouping of all the nucleic acid or amino acid sequences in a selected biochemical process of an organism. For example, a metabolic genotype is a grouping of all the nucleic acid and/or amino acid sequences of proteins involved in metabolism.

Methods for identifying metabolic genotypes have been described in the literature (see e.g. Edwards and Palsson 1999).

The database can be a flat file database or a relational database. The database can be an internal database, or an external database that is accessible to users, for example a public biological sequence database, such as Genbank or Genpept. An internal database is a database maintained as a private database, typically maintained behind a firewall, by an enterprise. An external database is located outside an internal database, and is typically maintained by a different entity than an internal database. A number of external public biological sequence databases are available and can be used with the current invention. For example, many of the biological sequence databases available from the National Center for Biological Information (NCBI), part of the National Library of Medicine, can be used with the current invention. Other examples of external databases include the Blocks database maintained by the Fred Hutchinson Cancer Research Center in Seattle, and the Swiss-Prot site maintained by the University of Geneva. Additionally, the external databases can include a database providing information regarding biochemical reactions, including databases of published literature references describing and analyzing biochemical reactions. Where a database included in the computer systems of the present invention is a public computer database that does not identify information that is relevant for a particular biochemical reaction network, the computer system either includes a function for performing biochemical reaction network reconstruction, or includes identification of the database entries that pertain to a particular biochemical reaction network. Additionally, there are several databases with biochemical pathway information, these databases include, for non-limiting example, EcoCyc, KEGG, WIT, and EMP. These databases can be used to provide the information to reconstruct the metabolic models.

In addition to the database discussed above, the computer system of the present invention includes a user interface capable of receiving a selection of one or more biochemical reaction networks for optimization and/or comparison, and capable of receiving a selection of an optimal performance. The interface can be a graphic user interface where selections are made using a series of menus, dialog boxes, and/or selectable buttons, for example. The interface typically takes a user through a series of screens beginning with a main screen. The user interface can include links that a user may select to access additional information relating to a biochemical reaction network.

The function of the computer system of the present invention that carries out the optimization methods typically includes a processing unit that executes a computer program product, itself representing another aspect of the invention, that includes a computer-readable program code embodied on a computer-usable medium and present in a memory function connected to the processing unit. The memory function can be, for example, a disk drive, Random Access Memory, Read Only Memory, or Flash Memory.

The computer program product that is read and executed by the processing unit of the computer system of the present invention, includes a computer-readable program code embodied on a computer-usable medium. The program code is capable of interacting with the database and effects the following steps within the computing system: providing an interface for receiving a selection of a desired performance of the networks; determining the desired optimal properties; displaying the results of the determination, and altering the biochemical reaction network, before recalculating optimal properties of the biochemical reaction network, and repeating the process until a desired performance is achieved. Altering the biochemical reaction network can be performed based on an alteration identified by a user, or can be performed automatically by the program code. The computer program can further provide an identification of database entries that are part of a reconstructed biochemical network, or can perform biochemical reaction network reconstruction. Furthermore, the computer program of the present invention can provide a function for comparing biochemical reaction networks to identify differences in components and properties.

The computer-readable program code can be generated using any well-known compiler that is compatible with a programming language used to write software for carrying out the methods of the current invention. Many programming languages are known that can be used to write software to perform the methods of the current invention.

As mentioned above, a method of this aspect of the invention can further include steps that involve adaptive evolution of a cultured strain to achieve the desired performance. Virtually any cell can be used with the methods of the present invention including, for example, a prokaryotic cell, or a eukaryotic cell such as a fungal cell or an animal cell including a cell of an animal cell line. However, a biochemical reaction network of the cell, or the cell of a closely related organism, must be sufficiently characterized to allow a high quality reconstruction of the comprehensive, substantially whole, and/or whole biochemical reaction network in a computer. Preferably, essentially the entire genome of the organism has been sequenced and genes encoding biomolecules, typically proteins, involved in the biochemical reaction network have been identified.

The genetic makeup of a cell can be constructed to contain the biochemical reactions that meet the desired performance to produce a cell with a potential to meet the desired performance. This can be achieved using the indigenous list of reactions in the cell and by adding and subtracting reactions from this list using genetic manipulations to achieve the reaction list capable of achieving the desired performance criteria, identified by the steps performed in silico described above. For example, reactions can be added or subtracted from the list by adding, changing, or deleting all or portions of one or more genes encoding one or more biomolecules involved in the reaction, for example by adding, changing, or deleting protein coding regions of one or more genes or by adding, changing, or deleting regulatory regions of one or more genes. In addition, for example, reactions can be added or subtracted from the list by altering expression of regulatory components (e.g., transcription factors) that effect the expression of one or more biomolecules involved in one or more reactions of the reaction list. The resulting engineered cell may or may not display the optimal properties calculated ahead of time by the in silico methods using the iterative optimization procedure described above.

Many methods exist in the art that describe the genetic manipulations of cells (see e.g., Datsenko K. A. and Wanner B. L., One-step inactivation of chromosomal genes in *Escherichia coli* K-12 using PCR products, *Proc. Natl. Acad. Sci. U.S.A.*, 97(12):6640-45 (2000); Link et al., Methods for generating precise deletions and insertions in the genome of wild-type *Escherichia coli*: Application to open reading frame characterization, *J. of Bacteriology*, 179:6228-37 (1997)). Any of the existing genetic manipulation procedures can be used to practice the invention disclosed.

After the cell has been constructed to have a potential to meet the desired performance, it is placed in culture under a specified environment. The specified environment is determined during the optimization procedure. That is, the optimization procedure calculates properties of the network under various environments, as described above, and identifies the specified environment in which the desired performance is achieved.

The cells are cultured for a sufficient period of time and under conditions to allow the cells to evolve to the desired performance. That is, adaptive evolution of natural or engineered strains is carried out as guided by the general optimization methods or procedures. Natural strains that have not experienced a particular environment or genetically altered strains can be analyzed by the network reconstruction and optimization procedures disclosed above. These strains can then be put under a selection pressure consistent with the desired function of the organisms and evolved towards the predetermined performance characteristics. The cells may achieve the desired performance without additional adaptive evolution. That is, the sufficient period of time for culturing the cells, may be immediately after the genetic makeup of the cells is constructed using the methods of the present invention without the need for further adaptive evolution.

In other words, Extended cultivation of a non-optimal or non-evolved strain can be performed to optimize or evolve the metabolic network toward the optimal solution that is achievable under the defined environmental conditions. The practice of this evolutionary process requires on the order of weeks to years to optimize a metabolic network depending on how far it is from the optimal conditions at the beginning of the evolutionary process, and how difficult it is to achieve the necessary changes through random mutation and shifts in regulation of gene expression. This process can be accelerated by the use of chemical mutagens and/or radiation. Additionally, the process is accelerated by genetically altering the living cell so that it contains the biochemical reactants determined by the in silico method described above, that achieve a desired performance.

Methods are known in the art for culturing cells under specified environmental conditions. For example, if the cell is *E. coli*, and the desired performance is a desired growth rate, the procedure set out below can be used. This procedure can be readily adapted for use with other bacterial cells and/or other performance criteria as is known in the art. Additionally, the procedures can be readily developed for use with other cell types such as animal cells. For example, the methods can be readily adapted for use with other culturing systems, such as large scales systems in which cells adhere to a culturing vessel. The culturing methods may be adapted for high-throughput analysis, as known in the art.

If a strain needs to be directionally evolved to achieve the desired performance, then following the construction of the metabolic reaction network in the chosen host strain, the cells are typically stored frozen at −80° C. with 30% glycerol. For each adaptive evolutionary process, frozen stocks are plated on LB agar and grown overnight at 37° C. From the plate, individual colonies can be identified that arose from a single cell. An individual colony can be used to inoculate a liquid culture, known as a pre-culture. Pre-cultures inoculated from a single colony of the respective strain are grown overnight in the defined medium for the subsequent evolutionary process. A pre-culture sample is taken the following day, typically at mid-log phase (in the middle of logarithmic growth) of growth to inoculate the culture conditions that define the environment that the adaptive evolution is to take place. Batch bioreactors or other suitable culture vessels are then initiated. This, typically would be done at 250 mL volumes in micro-carrier spinner flasks inside a temperature controlled incubator on top of a magnetic stir plate, set at suitable—typically high—speed to ensure sufficient aeration and at the optimal growth temperature (37° C. for wildtype *E. coli*) for any given strain. Other frequently used cultivation procedures known in the art can also be used.

After a suitable time period, typically the following day for *E. coli* (before the culture reaches stationary phase), an aliquot of the culture now in mid-log phase is serially transferred to a new spinner flask containing fresh medium. If the culture is being optimized for growth rate, stationary phase must be avoided to ensure that the selection criterion is growth rate. Then serial transfers are performed at fixed time intervals (typically every 24 hours depending on the growth rate) at mid-log phase and the volume of the inoculum into the new culture vessel is adjusted accordingly based on the increase in growth rate.

Growth rate is thus monitored frequently, typically on a daily basis in order to determine the proper volume of the inoculum to use for the next serial transfer. This serial cultivation process is repeated sufficiently often to allow the cells to evolve towards its optimal achievable growth under the conditions specified through the medium composition.

The growth and metabolic behavior is monitored during the adaptive evolutionary process to determine how the population is evolving over time. At fixed time intervals typically every few days, the culture is tested for metabolic and growth behavior, by measuring the oxygen uptake rate, substrate uptake rate and the growth rate. The results are then plotted as a data point on the phenotype phase plane. Movement of the so determined data point towards the line of optimality would indicate evolution towards optimal growth behavior. These measurements of the membrane transport fluxes along with the growth rate are repeated until we observe that the cells are operating their metabolic network such that the data points lie at the optimal conditions. The evolutionary process can then be continued until there is no further increase in the optimal performance, i.e., growth rate. If no further change is observed then we have achieved the maximal growth rate for the given conditions.

Byproduct secretion can be monitored by HPLC or other suitable methods of analytical chemistry to assess changes in metabolism that are implicated in the evolution towards optimal growth behavior. For these studies it is also imperative to determine a correlation of dry weight vs optical density for the evolved strain since this will be different from the wild-type. In addition to monitoring the growth rate and steady state growth, the cultures are inspected for any signs of possible contamination or co-evolution with a mutant subpopulation-aliquots for each day of culture are kept refrigerated as a backup in the event of any contamination, and the phenotype of the culture is ascertained by plating samples of the culture and inspecting for any differences in colony morphology or different mutants. On a daily basis, the optical density of the culture, time of inoculation, inoculum volume, growth rate, and any signs of contamination, are logged. Samples are also frozen at −80° C. in 30% glycerol for each day of culture for any possible further use.

After cells produced using the methods of the current invention evolve to achieve optimal performance, they may be further characterized. For example, a characterization can be made of the biochemical reaction network(s) of the cell. This characterization can be used to compare the properties, including components, of the biochemical reaction network (s) in the living cells to those predicted using the in silico methods.

The following examples are intended to illustrate but not limit the invention.

EXAMPLE 1

Detailed Methods for Determination of Optimal Function and Evolution for E. coli This example provides cultivation procedures that can be used to determine the optimality of strain performance and to carry out adaptive evolutionary processes.

Growth behavior of E. coli is determined by the following standard procedures. Growth is carried out in M9 minimal media (Maniatis et al., Molecular Cloning: A Laboratory Manual, (Cold Springs Harbor, N.Y., Cold Spring Harbor Laboratory, 545 (1982)) with the addition of the carbon source (Table 1). Cellular growth rate is varied by changing the environmental conditions, i.e. by changing the carbon source concentration approximately ranging between 0.05-4 g/L, temperature (27.5° C. to 37° C.), and oxygen (0-100% saturation relative to air). Batch cultures are set up in bioreactors at volumes of 250 mL in 500 mL flask with aeration. For these cultures the oxygen uptake rate (OUR) is monitored online, by either measuring the mass transfer coefficient for oxygen ($k_1a$), by using an off-gas analyzer, or by monitoring the oxygen tension in a respirometer chamber using known methods in the art. The temperature is controlled using a circulating water bath (Haake, Berlin, Germany). All measurements and data analysis are restricted to the exponential phase of growth. The biomass and the concentration of the substrate and metabolic by-products in the media are monitored throughout the experiment using methods known in the art. Cellular growth is monitored by measuring the optical density (OD) at 600 nm and 420 nm and by cell counts. OD to cellular dry weight correlations are determined by two different methods; (1) 50 mL samples of culture are spun down and are dried at 75° C. to a constant weight, and (2) 25 ml (taken throughout the culture) samples are filtered through a 0.45 um filter and dried to a constant weight. The concentration of metabolites in the culture media is determined by HPLC. An aminex HPX-87H ion exchange carbohydrate-organic acid column (@66° C.) is used with degassed 5 mM $H_2SO_4$ as the mobile phase and UV detection. Enzymatic assays are also used to determine the substrate uptake rate and by-product secretion rates. The dissolved oxygen in the culture is monitored using a polarographic dissolved oxygen probe. Oxygen consumption is measured by three different methodologies; (1) passing the effluent gas through a 1440C Servomex oxygen analyzer (Servomex Co., Inc. Norwood, Mass.), (2) calculated from the dissolved oxygen reading and $k_{1a}$ measurements, and (3) in a respirometer chamber in a separate 50 ml flask. All three methods used for measuring the oxygen uptake rate give similar and reproducible results.

The cultivation procedures provided in this Example can be used to determine the optimality of strain performance and to carry out adaptive evolution.

TABLE I

| M9 Minimal Media (Per liter) | |
| --- | --- |
| 5 × M9 Salts | 200 mL |
| 1M $MgSO_4$ | 2 mL |
| 20% Solution of Carbon Source | 20 mL |
| 1M CaCl | 0.1 mL |
| 5 × M9 Salts (Per liter) | |
| $Na_2HPO_4 * 7H_2O$ | 64 g |
| $KH_2PO_4$ | 15 g |

TABLE I-continued

| M9 Minimal Media (Per liter) | |
| --- | --- |
| NaCl | 2.5 g |
| $NH_4Cl$ | 5.0 g |

EXAMPLE 2

Calculation of Optimally Properties and Phenotypic Phase Planes

This example shows how we calculate the optimality properties of the reconstructed network and how such results are represented on a phenotypic phase plane.

The capabilities of a metabolic network can be assessed using flux balance analysis (FBA) (Bonarius et al., (1997); Edwards et al., (1999); Varma et al., (1994a); Varma et al., (1994b)). FBA is primarily based on the conservation of mass in the metabolic network. The conservation requirement is implemented by stoichiometric balance equations; thus, FBA relies on the stoichiometric characteristics of the metabolic network.

The flux balance equation is $S \cdot v = b^v$, where S is the stoichiometric matrix, the vector v defines the metabolic fluxes, and $b^v$ is nominally zero—thus, enforcing simultaneous mass, energy, and redox balance constraints through a set of mass balances. Variations of the $b^v$ vector from zero were used in the shadow price analysis (discussed below). In the E. coli metabolic network, the number of metabolic fluxes was greater than the number of mass balances, thus leading to a plurality of feasible flux distributions that lie in the null space of the matrix S. Additional constraints were also placed on the feasible value of each flux in the metabolic network ($\alpha_i \leq v_i \leq \beta_i$). These constraints were utilized to define the reversibility of the internal reactions and to set the uptake rate for the transport reactions. The transport of inorganic phosphate, ammonia, carbon dioxide, sulfate, potassium, and sodium were unrestrained; whereas the uptake of the carbon source and oxygen were restrained as specified. All metabolic by-products (i.e. acetate, ethanol, formate, pyruvate, succinate, lactate, etc) which are known be transported out of the cell were always allowed to leave the metabolic system. In this analysis, $\alpha_i$ for the internal fluxes was set to zero for all irreversible fluxes and all reversible fluxes were unbounded in the forward and reverse direction (the reversibility of each reaction is defined on the website of supplementary information). The intersection of the null space, and region defined by the linear inequalities, defined the capabilities of the metabolic network and has been referred to as the flux cone (Schilling et al., 1999).

The determination of the optimal metabolic flux distribution that lies within the flux cone was formulated as a linear programming (LP) problem, in which the solution that minimizes a particular metabolic objective was identified (Bonarius, H. P. J. et al., Metabolic flux analysis of hybridoma cells in different culture media using mass balances, *Biotechnology and Bioengineering* 50: 299-318 (1996); Edwards et al., (1999); Pramanik et al., (1997); Varma et al., (1994a); Varma et al., (1994b)). The growth flux was defined as the objective. The growth flux was defined as a metabolic flux utilizing the biosynthetic precursors, $X_m$, in the appropriate ratios, $$\sum_{all\ m} d_m \cdot X_m \xrightarrow{v_{growth}} Biomass,$$

where $d_m$ is the biomass fraction of metabolite $X_m$. The biomass composition was defined based on the literature (Neidhardt, F C, Ed., *Escherichia coli* and *Salmonella*: cellular and molecular biology (ASM Press, Washington, D.C., 1996); Neidhardt, F C, Umbarger, H E, in *Escherichia coli* and *Salmonella*: cellular and molecular biology F. C. Neidhardt, Ed. (ASM Press, Washington, D.C., 1996), vol. 1, pp. 13-16 (1996)).

All steady state metabolic flux distributions are mathematically confined to the flux cone defined for the given metabolic map, where each solution in the flux cone corresponds to a particular internal flux distribution or a particular metabolic phenotype (Varma et al., 1994a; Varma et al., 1994b)). Under specified growth conditions, the optimal phenotype in the cone can be determined using linear programming (LP). If the constraints vary, the shape of the cone changes and the optimal flux vector may qualitatively change; for example, inactive fluxes may be activated and vice versa. The phase plane analysis is developed to consider all possible variations in two constraining environmental variables.

Defining Phenotype Phase Planes (PhPPs): Uptake rates of two nutrients (such as the carbon substrate and oxygen) were defined as two axes on an (x,y)-plane, and the optimal flux distribution was calculated for all points in this plane. There are a finite number of qualitatively different optimal metabolic flux maps, or metabolic phenotypes, present in such a plane. The demarcations on the phase plane were defined by a shadow price analysis (Varma, A, Boesch, B W, Palsson, B O., Stoichiometric interpretation of *Escherichia coli* glucose catabolism under various oxygenation rates, *Applied and Environmental Microbiology* 59, 2465-73 (1993); Varma, A, Palsson, B O., Metabolic capabilities of *Escherichia coli*: II. Optimal growth patterns. *Journal of Theoretical Biology* 165, 503-522 (1993)). This procedure led to the definition of distinct regions, or "phases", in the plane, for which the optimal use of the metabolic pathways was qualitatively different. Each phase was written as $Pn_{x,y}$, where P represents phenotype, n is the number of the demarcated region for this phenotype (as shown in the corresponding FIG. 1), and x,y the two uptake rates on the axis of the plane.

Calculating the Phase Plane: The phase planes were constructed by calculating the shadow prices throughout the two-parameter space, and lines were drawn to demarcate regions of constant shadow prices. The shadow prices defined the intrinsic value of each metabolite toward the objective function. Changes in shadow prices were used to interpret of metabolic behavior.

Mathematically, the shadow prices are defined as, $$\gamma_i = -\frac{dZ}{db_i^v} \qquad (1)$$

and are associated with each metabolite in the network. The shadow prices defined the sensitivity of the objective function (Z) to changes in the availability of each metabolite ($b_i^v$ defines the violation of a mass balance constraint and is equivalent to an uptake reaction). The shadow prices were either negative, zero, or positive, depending on the value of the metabolite. The direction and magnitude of the shadow price vector in each region of the phase plane was different (by definition of the phase plane); thus, the state of the metabolic system was different in each region.

Isoclines: Isoclines were also defined to interpret the metabolic phenotype. Isoclines were defined to represent the locus of points within the two-dimensional space that provide for the same value of the objective function. The slope of the isoclines within each region was calculated from the shadow prices; thus, by definition the slope of the isoclines was different in each region of the PhPP. A ratio of shadow prices was used to define the slope of the isoclines ($\rho$):

$$\rho = -\frac{\gamma_x}{\gamma_y}\bigg|_Z = -\left(\frac{-dZ/db_x^v}{-dZ/db_y^v}\right)\bigg|_Z = -\frac{db_y^v}{db_x^v}\bigg|_Z \qquad (2)$$

The negative sign in Eqn. 2 was introduced in anticipation of its interpretation. The condition dependent relative value of the substrates, defined as $\rho$, was used to interpret the constraining factors on the metabolic network. In regions where $\rho$ was negative, there was dual limitation of the substrates. Under different condition, the isoclines were also either horizontal or vertical in certain phase plane regions, representing regions of single substrate limitation, the $\rho$ value in these regions was zero or infinite, respectively. Certain regions in the PhPP also had a positive $\rho$; these regions were termed "futile" regions, and increased uptake of one of the substrates had a negative effect on the objective function in these regions. Finally, due to stoichiometric limitations, there were infeasible steady state regions in the PhPP.

Line of Optimality: The line of optimality (LO) was defined as the line representing the optimal relation between the two metabolic fluxes corresponding to the axis of the PhPP. For results presented herein, this line can be interpreted as the optimal oxygen uptake for the complete oxidation of the substrate in order to support the maximal biomass yield.

These procedures were applied to the reaction list for *E. coli* K-12 defined by (Edwards and Palsson, The *Escherichia coli* MG1655 in silico metabolic genotype: its definition, characteristics, and capabilities, *Proc. Natl. Acad. Sci. U.S.A.*, 97(10):5528-33 (200b)). It generates the two and three dimensional phase planes that are used in the examples below.

EXAMPLE 3

Optimal Behaviour of *E. coli* Under Defined Conditions

This Example shows that the strain used exhibited optimal aerobic growth using acetate and succinate as primary substrates without adaptive evolution.

The list of metabolic reactions that take place in *E. coli* K-12 M1655 has been assembled (Edwards and Palsson (2000b)). Based on this list a stoichiometric matrix was formulated. Using maximal uptake rates for oxygen (on the y-axis) and a carbon substrate (on the x-axis) a phenotypic phase plane was calculated using the procedures described above. Specifically two carbon sources were used, acetate and succinate. Then the calculated phase planes were used to determine the optimal growth conditions and a series of growth experiments were performed. The computational (i.e. in silico) and experimental results were then compared.

Acetate. Optimal growth performance on acetate was investigated in silico, and the predictions generated were compared to experimental data. The in silico study started with a phenotype phase plane (PhPP) analysis with the acetate and oxygen uptake rates defined as the axes of the two-dimensional projection of the flux cone representing the capabilities of *E. coli* metabolism (FIG. 1). The flux cone is the region of all admissible steady state metabolic flux distributions (for a complete description of the flux cone see ref (Schilling et al., Metabolic pathway analysis: basic concepts and scientific applications in the post-genomic era, *Biotechnol. Prog.*, 15(3):296 (1999)). Furthermore, a three-dimensional projection of the flux cone with the growth rate defined as the third dimension was utilized (FIG. 1). The in silico analysis of the acetate-oxygen PhPP has been described in Example 2 above. The optimal (with respect to cellular growth) relation between the acetate and oxygen uptake rate, and this line is referred to as the line of optimality (LO).

The PhPP was used to analyze and interpret the operation of the metabolic network. For example, under oxygen limitations the characteristics of the metabolic network may be defined by region 2 of the PhPP (FIGS. 1 & 2), where the acetate uptake rate exceeds the optimal relation to the oxygen uptake rate. From FIG. 1, it can be seen that if the metabolic network were operating within region 2, the optimal capability to support growth would be increased by reducing the acetate uptake rate to a point on the LO. A similar interpretation can be made for points within region 1, with oxygen and acetate switching roles. Hence, metabolic flux vectors defining a point in region 1 or region 2 would indicate inefficient utilization of the available resources. Thus, the in silico PhPP analysis led to the conclusion that if the regulation of the *E. coli* metabolic network has evolved to operate optimally to support growth with acetate as the sole carbon source, the relation between the acetate and oxygen uptake rate and the growth rate should be defined by the LO (FIGS. 1 & 2).

The relation between the acetate and oxygen uptake rates and the growth rate was experimentally examined by cultivating *E. coli* MG1655 on acetate minimal medium. The acetate uptake rate was experimentally controlled by changing the acetate concentration in the minimal media. The uptake rates of acetate and oxygen and the growth rate were measured and the experimental points were plotted on the PhPP (FIGS. 1 and 2). The calculated optimal relation between the acetate and oxygen uptake rate was then compared to the experimental data (FIG. 1). Comparison of the experimental data to the in silico predictions indicated a 14% difference between the slope (0.91) of the linear regression line for the experimental data and the slope (1.04) of the in silico defined LO for aerobic growth on acetate minimal media.

Figure 2:
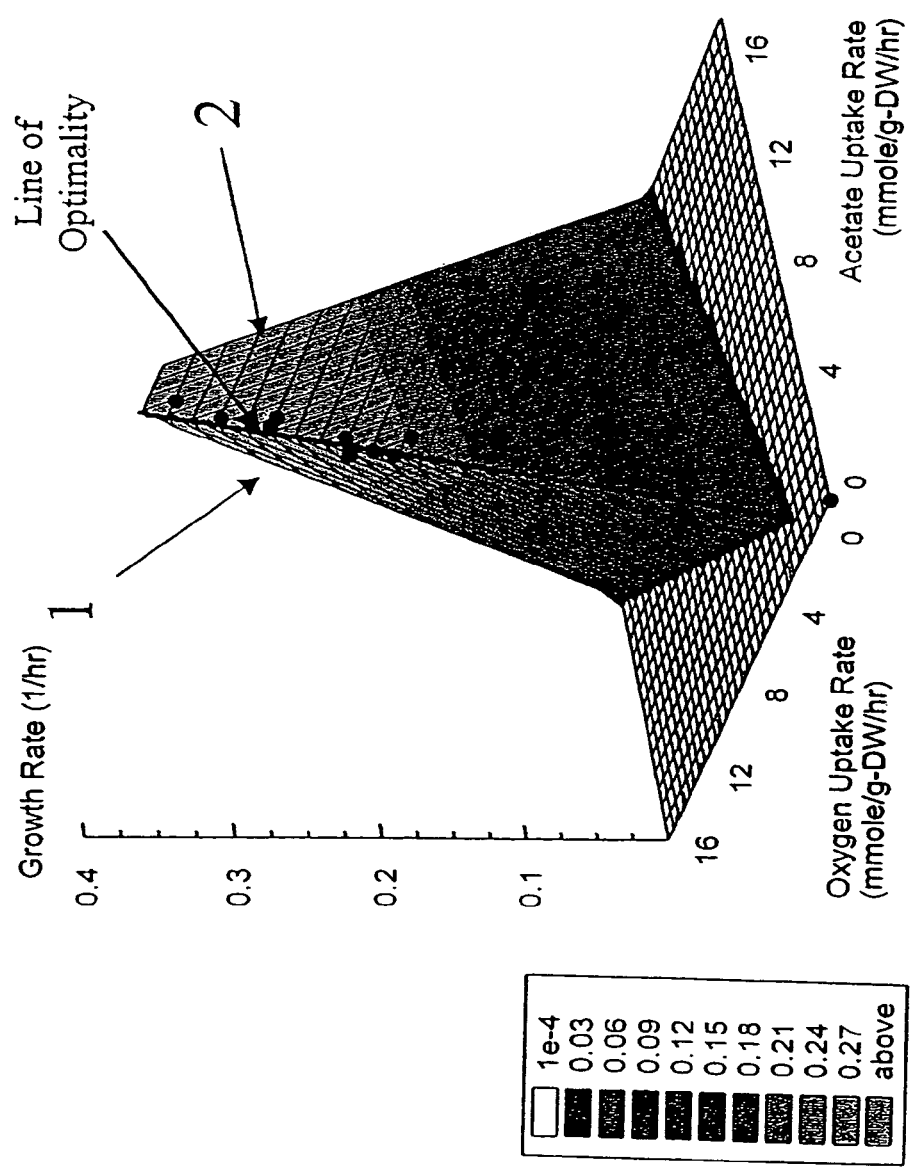
FIG. 2: The three-dimensional rendering of the phase surface for growth of *E. coli* on acetate. The x and y axis represent the same variables as in FIG. 1. The third dimension (the z-dimension) represents the cellular growth rate. The z-axis values are in gray scale with the optimal growth rate value quantitatively indicated on the corresponding legend. The line of optimality (LO) in three-dimensions is indicated. The parametric equation of LO in three-dimensions is indicated in the text. The black lines define the surface of the metabolic capabilities in the three-dimensional projection of the flux cone and represent constant values of the acetate uptake rate or oxygen uptake rate. The quantitative effect on cellular growth potential of increasing the acetate uptake rate (without proportional increase in the oxygen uptake rate) can be visualized. The data points are also plotted on the three-dimensional figure and error bars have been omitted.

The measured and calculated growth rates were plotted as the third-dimension above the acetate-oxygen PhPP (FIG. 2). The color-coded surface represents the three-dimensional projection of the flux cone. In other words, the color-coded surface defines the solution space, and all feasible steady state metabolic flux distributions are confined within the surface. Yes we can. The LO on the two-dimensional phase plane (FIG. 1) is a projection of the edge on the three-dimensional surface on to the x,y-plane (acetate uptake rate, oxygen uptake rate). The experimental data were plotted in the three-dimensional space (FIG. 2). To quantitatively visualize the proximity of the data points to the LO in three-dimensions, the in silico predictions and the experimental data were projected onto each plane formed by the basis vectors.

Figure 3:
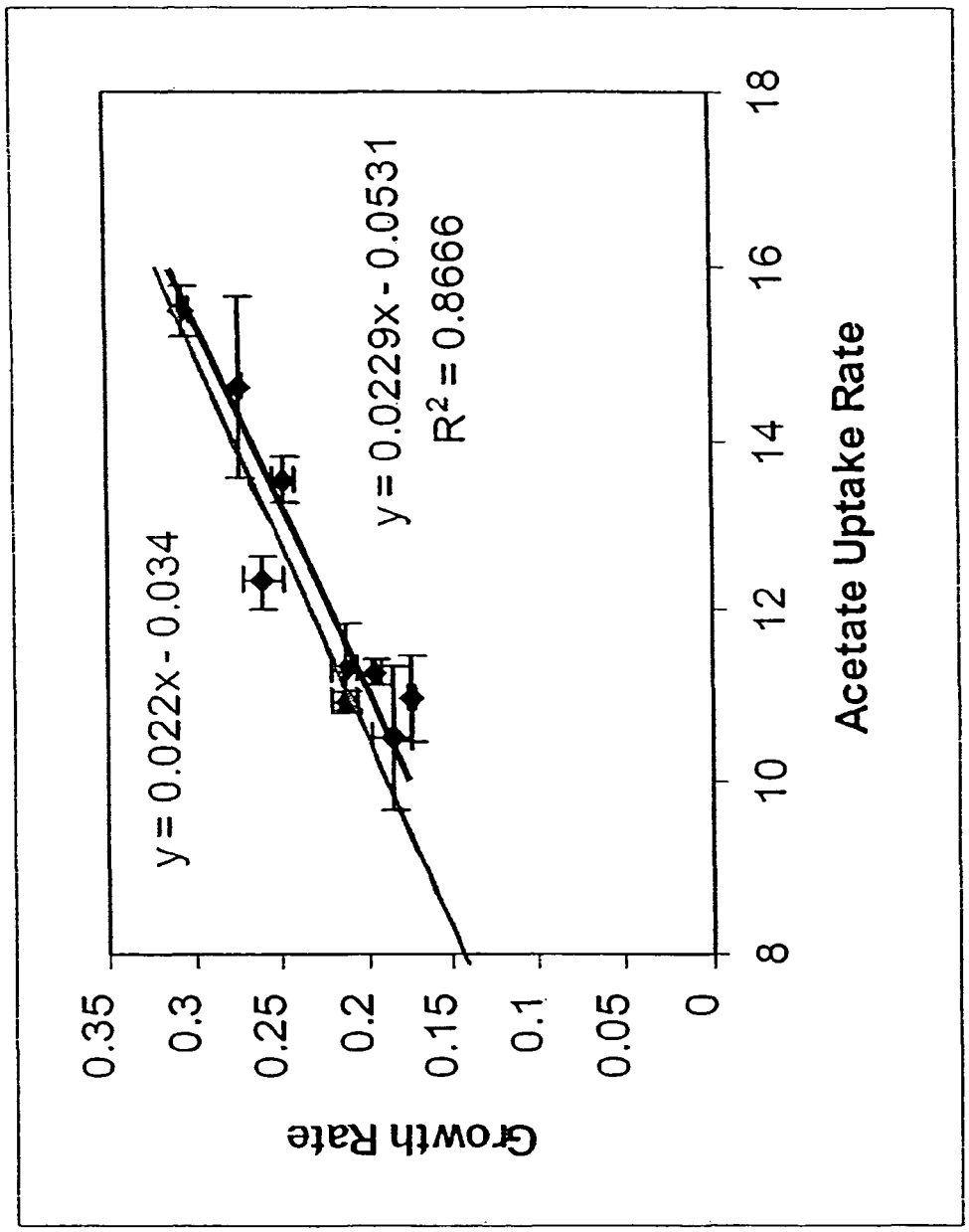
FIG. 3: Line of optimality for growth on acetate projected onto a plane formed by the acetate uptake rate and the growth rate. The data points have also been projected and a linear regression was performed in the two-dimensional plane to experimentally define the line of optimality. The line of optimality is indicated as a gray line and the regression line as a black line.
Figure 4:
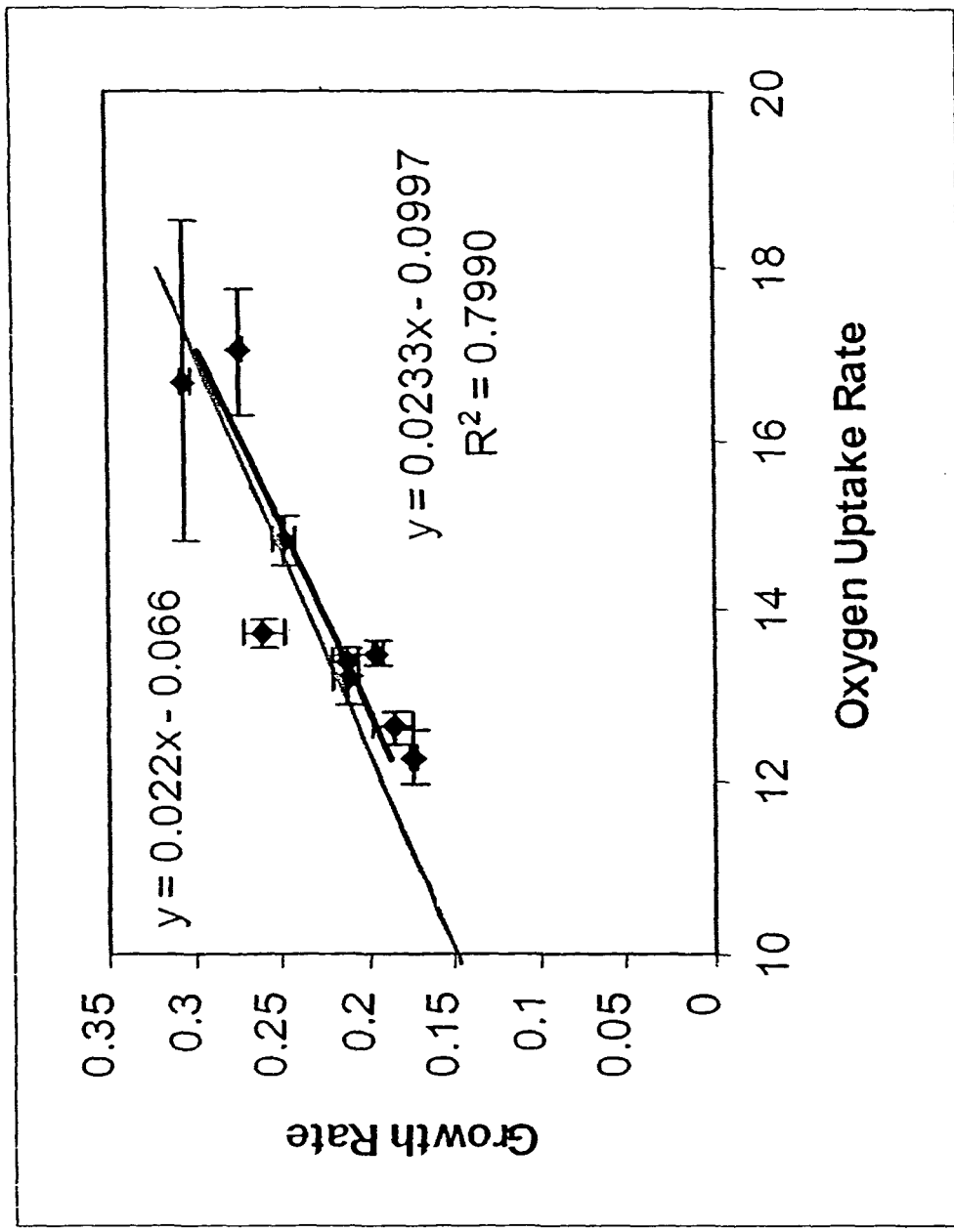
FIG. 4: Line of optimality for growth on acetate projected onto a plane formed by the oxygen uptake rate and the growth rate. The data points have also been projected and a linear regression was performed in the two-dimensional plane to experimentally define the line of optimality. The line of optimality is indicated as a gray line and the regression line as a black line.

The projection of the three-dimensional LO and the experimental data points onto the (x,y), (x,z), and (y,z) (x-axis: acetate uptake rate; y-axis: oxygen uptake rate; z-axis: growth rate) planes is indicated in FIGS. 3 & 4 respectively, where the quality of the linear regression is indicated by the correlation coefficient, and the data are compared to the in silico predictions. The predicted and the observed metabolic fluxes (substrate and oxygen uptake rates and growth rate) for each point were directly compared and the in silico predictions and had an overall average error of 5.8%. At this point, we should note that the information used to reconstruct the metabolic network was obtained independent from the present experiments (Edwards and Palsson, (2000b)). The calculated PhPP represents a priori interpretation and prediction of the data obtained in the present study.

Succinate. The succinate-oxygen PhPP (FIG. 5) was more complicated than the acetate-oxygen PhPP. The succinate-oxygen PhPP (FIG. 5) had 4 distinct regions of qualitatively distinct optimal metabolic network utilization. Regions 1 and 4 of the succinate-oxygen PhPP were analogous to regions 1 and 2 of the acetate-oxygen PhPP. For example, it can be seen from FIG. 5 that the maximal growth flux for a flux vector in region 4 can be increased if the succinate uptake is reduced to a point defined by the region 3,4 demarcation. Furthermore, from the PhPP analysis, region 3 is defined as a single substrate limited region. The single substrate limited region indicates that the succinate uptake rate has little effect on the maximal growth flux in region 3, whereas the oxygen uptake rate has a positive effect on the growth rate.

Region 2 is defined as a dual substrate limited region, since in region 2 the metabolic network can support an increased growth rate if the succinate uptake rate is increased. The in silico analysis shows that the cellular growth rate can be increased by operating the metabolic network off of the LO in region 2, by implementing a partially aerobic metabolism and the secretion of a metabolic by-product. The optimal metabolic by-product was calculated to be acetate. The production of a reduced metabolic by-product in region 2 however reduces the overall biomass yield. Therefore, based on the PhPP analysis, it may be surmised that, if the regulation of the metabolic network evolved toward optimal growth with succinate as the sole carbon source, the metabolic network will operate with a flux vector along the LO. However, the growth rate can be increased by moving the flux vector into region 2, thus we expect that the network should only operate in region 2 when oxygen is limited and succinate is plentiful if the stated hypothesis is true.

Figure 5:
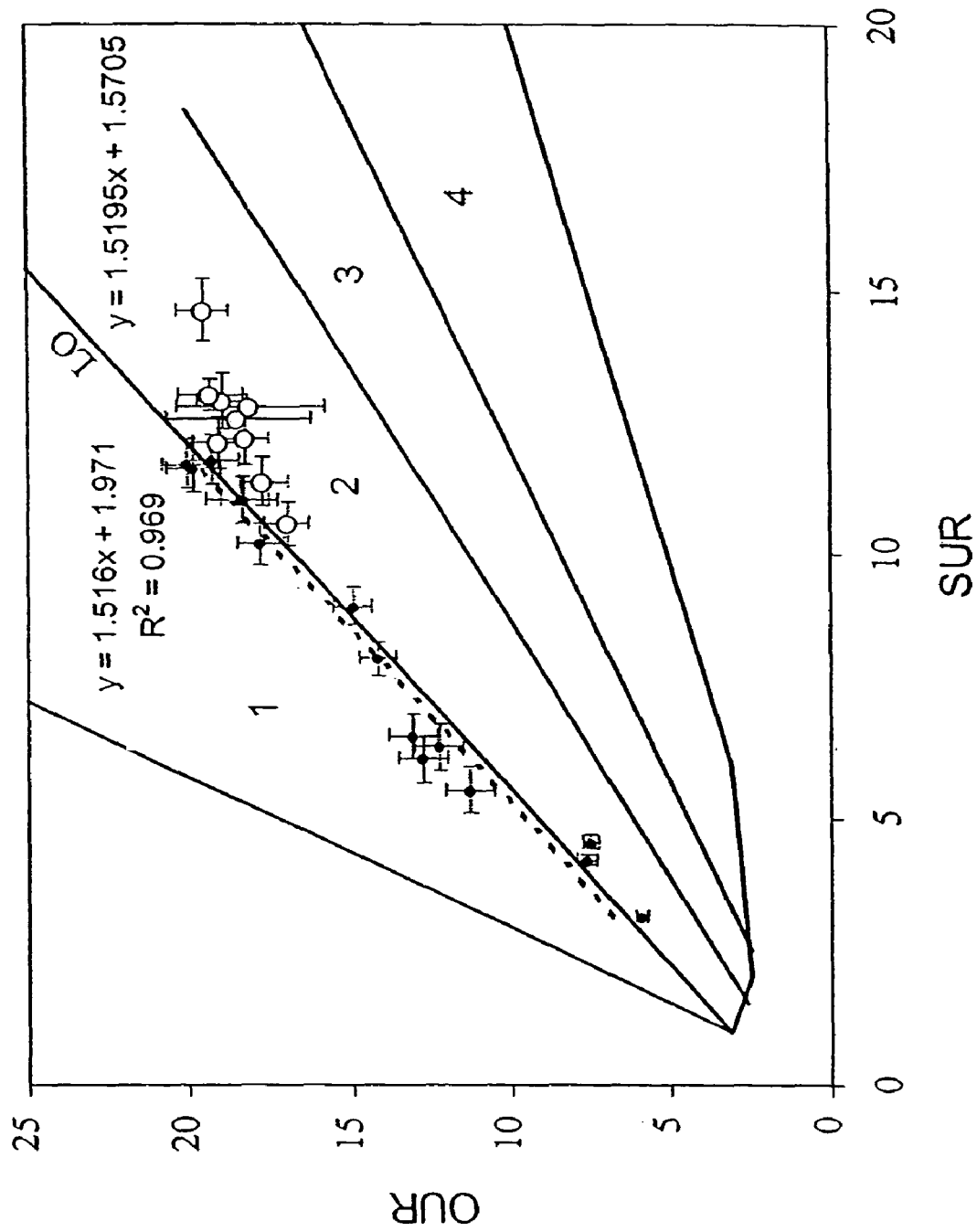
FIG. 5: The succinate uptake rate (mmole/g-DW/hr) versus oxygen uptake rate (mmole/g-DW/hr) represented in the phenotype phase plane. The labeled line is the in silico defined line of optimality (LO). The experimental data points are displayed on the figure. The error bars are displayed for both the succinate and oxygen uptake rate measurements and represent a single standard deviation. Cultivations for which acetate was produced above a threshold of 0.3 mmole/gDW/hr are indicated by open circles, filled circles identify either no acetate production or production below the threshold. The black dotted line represents the linear regression of the data points with no acetate production.

*E. coli* growth experiments on succinate minimal M9 media were performed to critically test the hypothesis given the above in silico analysis. Multiple batch cultures were grown at various succinate concentrations and temperatures to span a range of succinate uptake rates. The aeration and agitation were held constant to maintain a consistent maximal oxygen diffusion rate in all the cultures. The succinate and oxygen uptake rates and the growth rate were measured separately for each independent growth experiment. The experimental data were then directly compared to the in silico predictions (FIG. 5).

Figure 6:
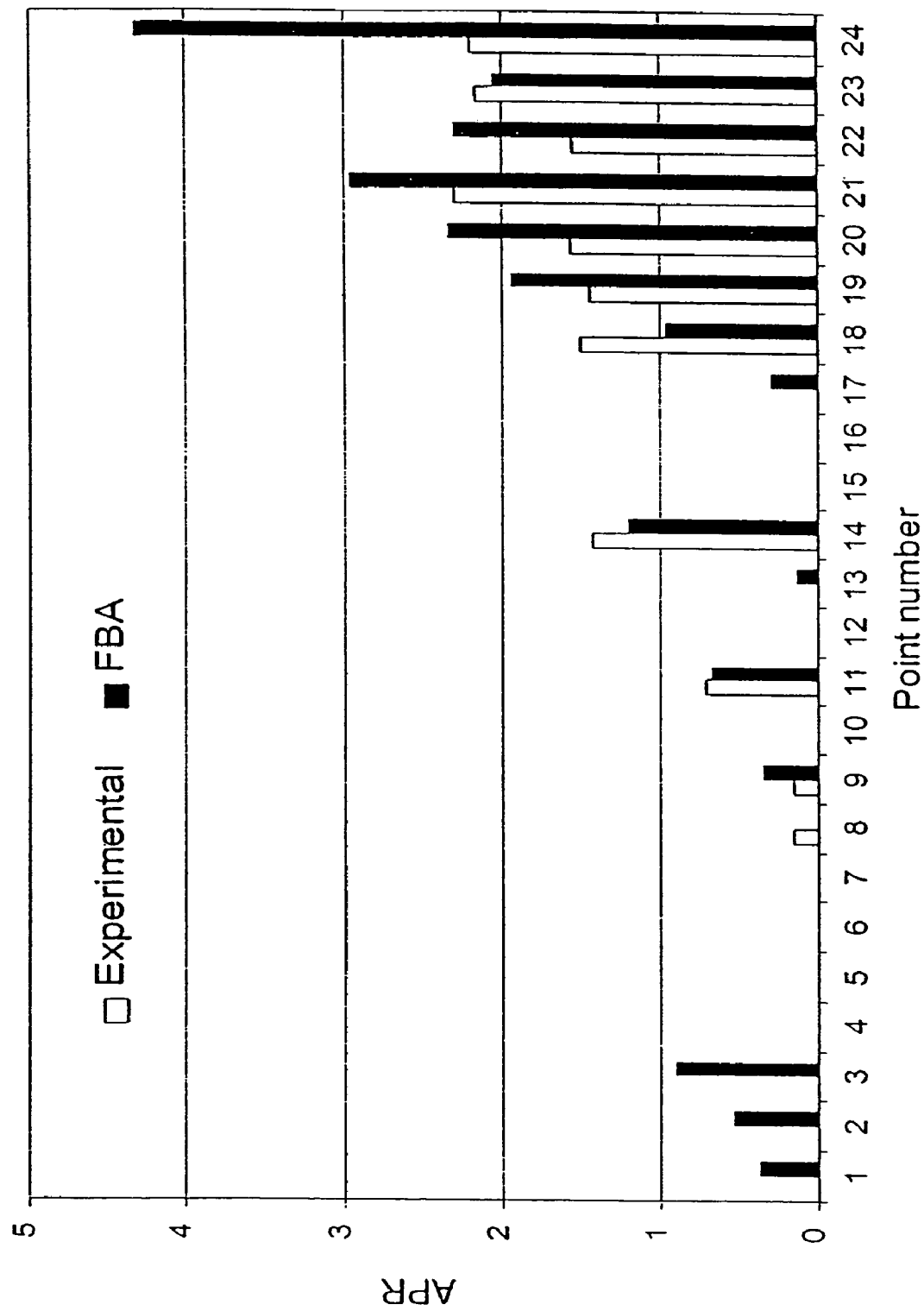
FIG. 6: The measured acetate production vs. the in silico predictions for each point illustrated in FIG. 5. The data points are rank ordered by the magnitude of the succinate uptake rate.

The experimental data points were consistent with the stated hypothesis: the flux vector consistently identified points along the LO for oxygen uptake rates below a critical value (~18.8 mmole-g-DW-1·hr-1). Furthermore, the cultures that identified points along the LO produced little or no acetate as a metabolic by-product (as predicted by the in silico analysis—see FIG. 5). As hypothesized, the experimental data indicates horizontal movement of the flux vector within region 2 for the experimental systems that are oxygen limited but have plentiful succinate. The break point in the experimental data was determined to correspond to a maximal oxygen uptake rate of 18.8±0.5 mmole*gDW-1*hr-1. Flux vectors within regions 3 or 4 were never observed. Acetate production was measured for the cultures identified in region 2, and the acetate production is quantitatively compared to the in silico predictions in FIG. 6.

Figure 7:
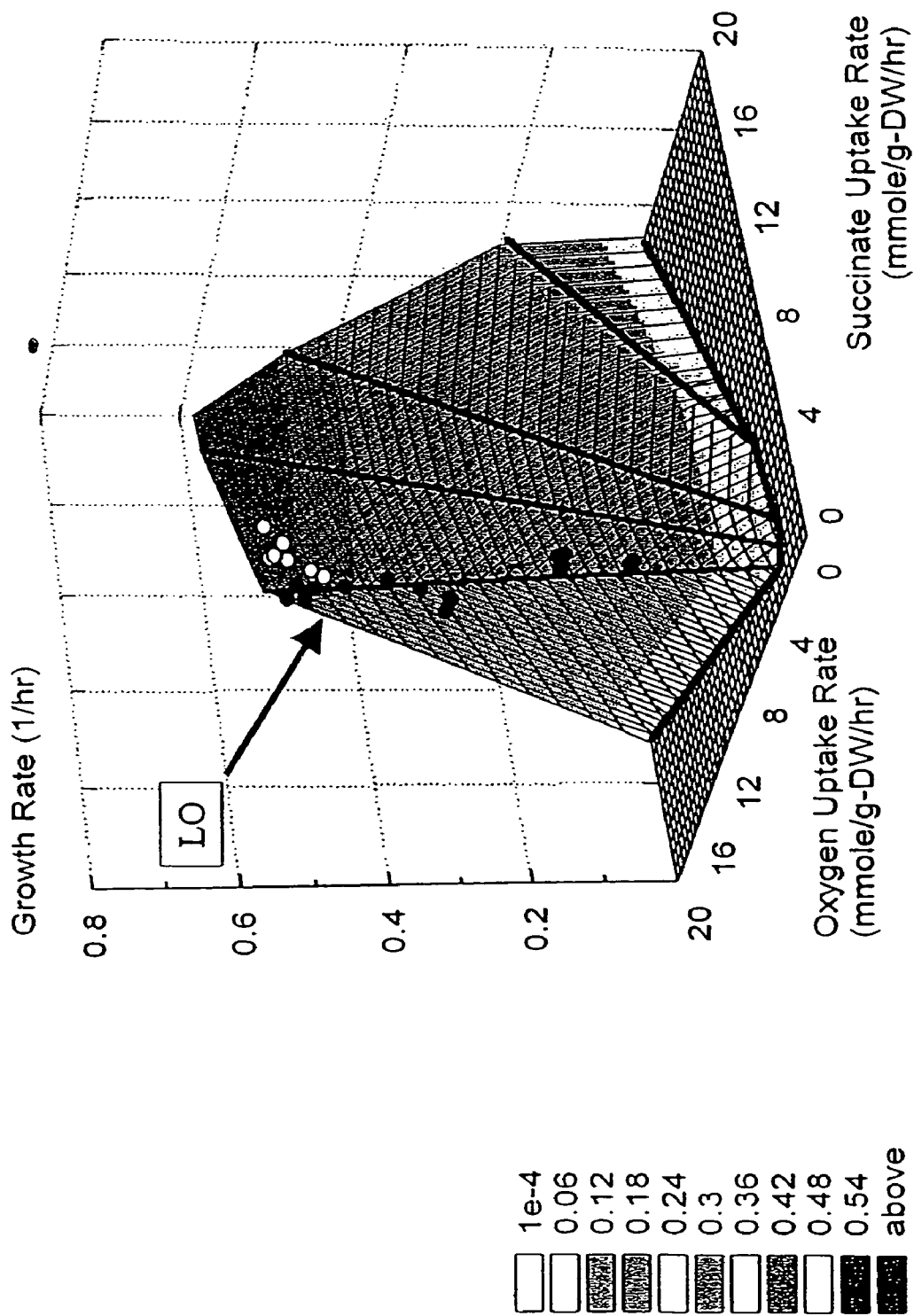
FIG. 7: Three-dimensional phenotype phase plane for *E. coli* growth on succinate. The x and y axis represent the same variables as in FIG. 6. The third dimension (the z-axis) represents the cellular growth rate. The z-axis values are in gray scale with the corresponding legend in the figure. The demarcation lines separating the colored regions represent constant oxygen and acetate uptake rates, and the quantitative effect of moving away from the line of optimality can be visualized. The data points are plotted in this three-dimensional figure with the exception of the error bars.

The optimal growth rate surface was constructed over the succinate-oxygen PhPP, and the measured flux vectors fell near the edge of the polytope that corresponded to the LO (FIG. 7). The flux vectors also identified a locus of points on the phase surface in region 2 with a constant oxygen uptake rate equal to the maximal oxygen uptake limit of the system. To quantitatively test the predictive capability of the in silico analysis and the in silico derived hypothesis, we employed a piecewise linear model to describe our hypothesis and the experimentally observed flux vectors. The piecewise linear model is defined as follows: we identified the locus of points defined by the flux vector for a range of succinate uptake rates and an oxygen uptake limit. Below the oxygen uptake limit, the locus of points lies along the LO, and above the oxygen uptake limit the locus of points lies along the phase surface with a constant oxygen uptake rate (the oxygen uptake limit). Based on the piecewise linear model, the succinate uptake rate was used to predict the oxygen uptake rate and the growth rate, and the other two permutations were also considered. From this analysis an overall average error between the in silico predictions and the experimental data was 10.7%.

This Example shows that the strain used exhibited optimal aerobic growth using acetate and succinate as primary substrates. No adaptive evolution was necessary to achieve this optimal performance.

EXAMPLE 4

Evolution of a Sub-Optimal *E. coli* Strain to Optimally

This Example demonstrates that *E. coli* can undergo some phenotypic adaptation from a sub-optimal growth state to an optimal state determined in silico.

Figure 8:
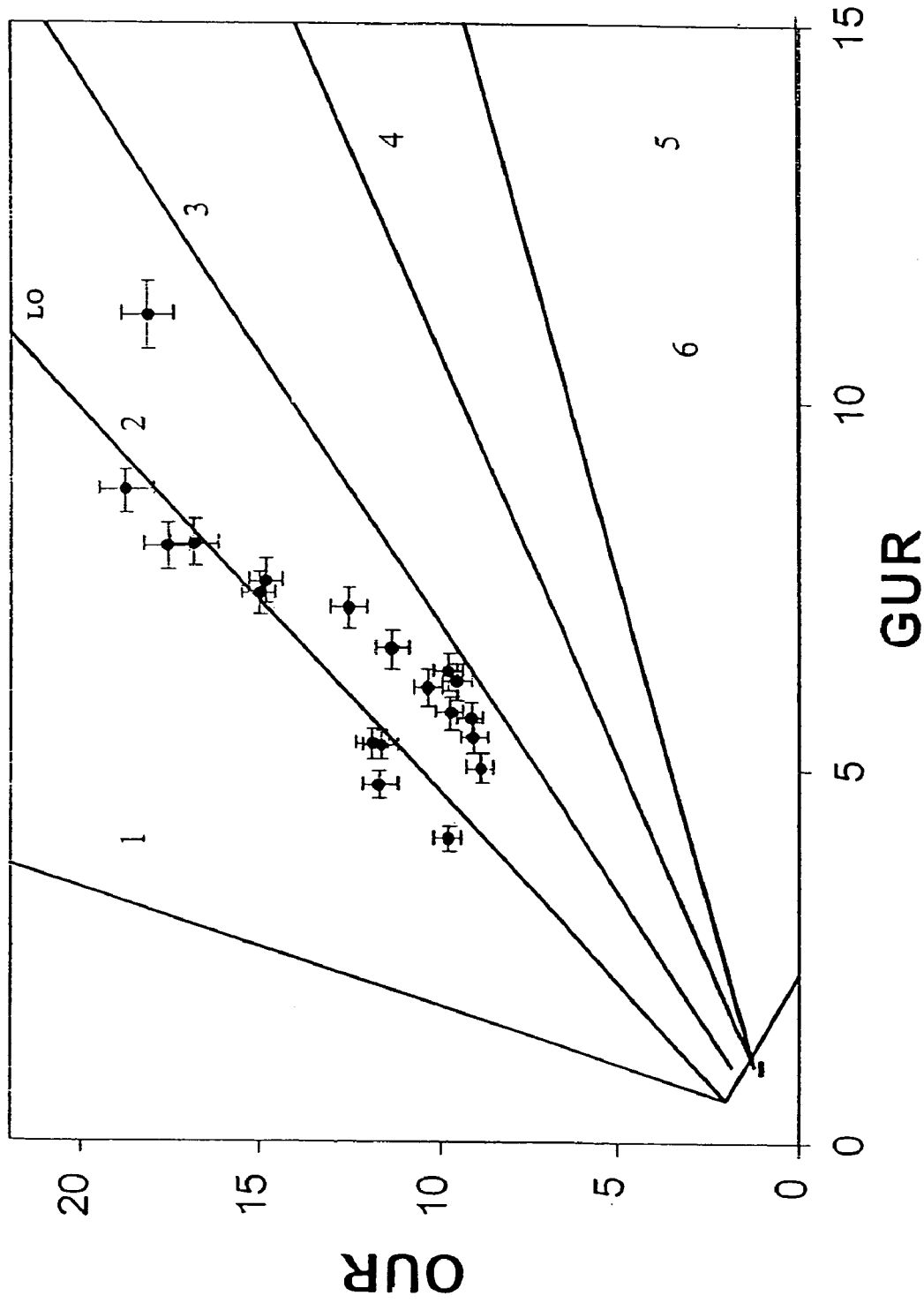
FIG. 8: Calculated and experimental values for growth of *E. coli* K-12 on glucose. The glucose uptake rate, GUR (mmole/gDW/h), and the oxygen uptake rate, OUR (mmole/gDW/h), are shown in the phenotype phase plane. The LO is indicated. Data points are confined to the LO or the acetate overflow region, where acetate secretion is predicted in silico and experimentally observed.

Glucose: The glucose-oxygen PhPP contains six distinct regions (FIG. 8) Like the succinate-oxygen PhPP, region 1 represents futile cycles and sub-optimal growth performance, whereas region 2 is characterized by acetate overflow metabolism. The two are separated by the LO.

As before, the cellular growth rate, OUR, and glucose uptake rate (GUR) were experimentally determined over a range of glucose concentrations and temperatures. Most experimentally determined values for the GUR, OUR, corresponded to points on the LO or slightly in region 2 of the PhPP (FIG. 8), where the predicted acetate secretion was experimentally observed.

Figure 9:
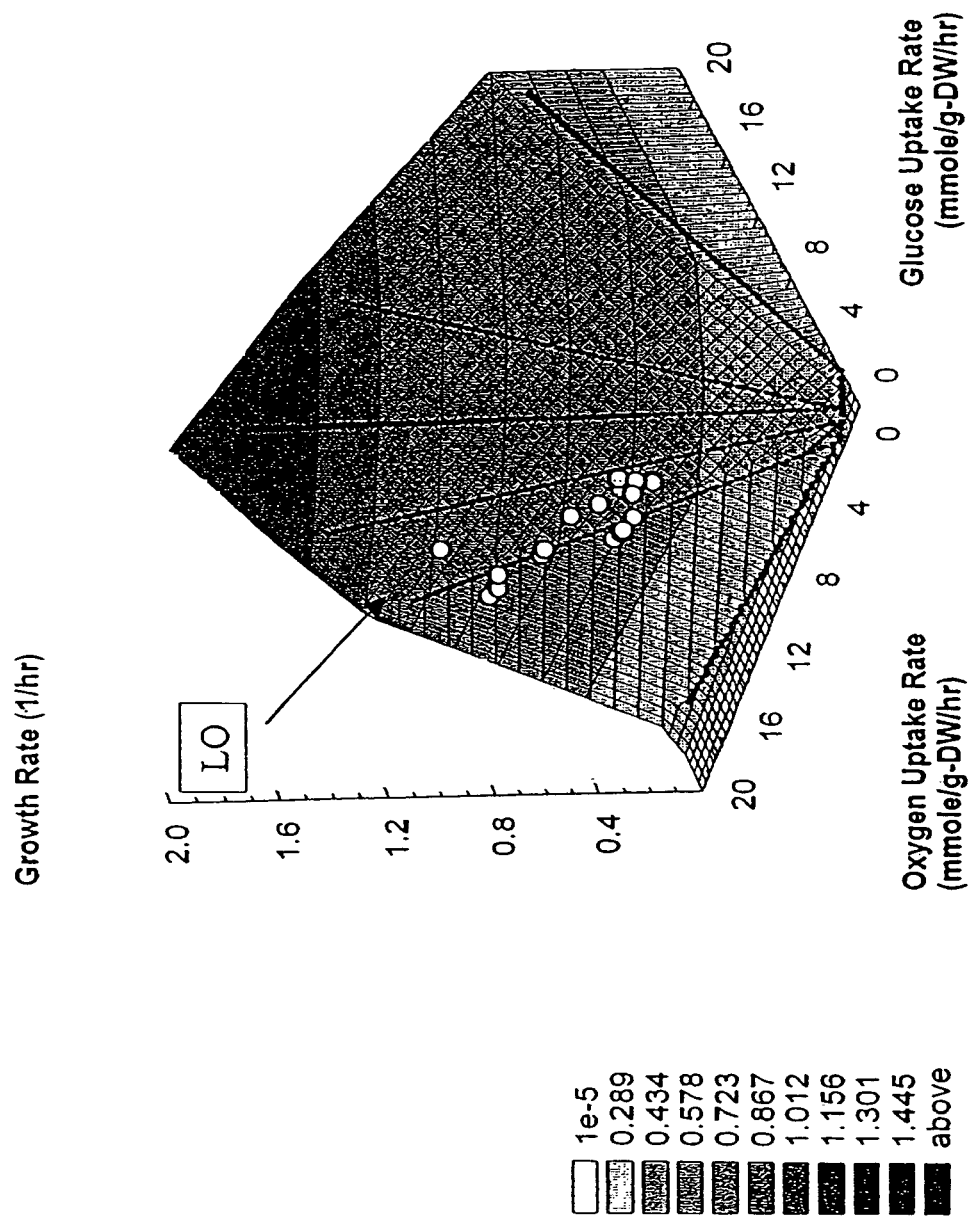
FIG. 9: Three-dimensional rendering of growth rates graphed over the phase plane for growth on glucose. The x and y axes represent the same variables as in FIG. 8. The z-axis represents the cellular growth rate, with shaded-coded values and the optimal growth rate indicated on the legend.
Figure 10:
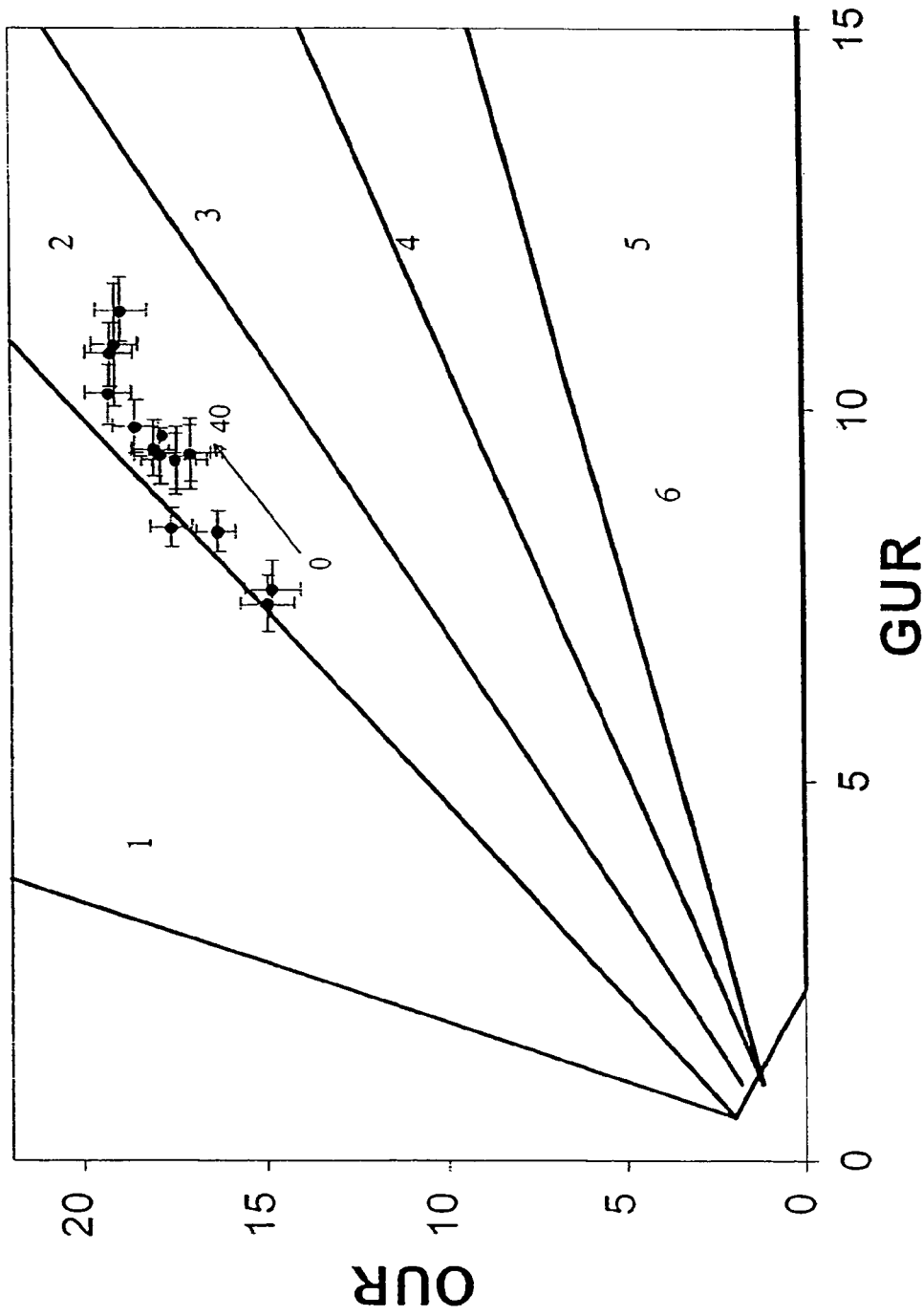
FIG. 10: GUR plotted against OUR with experimental values for adaptive evolution experiments. Data points lie near the LO and in region 2 where acetate overflow is predicted.
Figure 11:
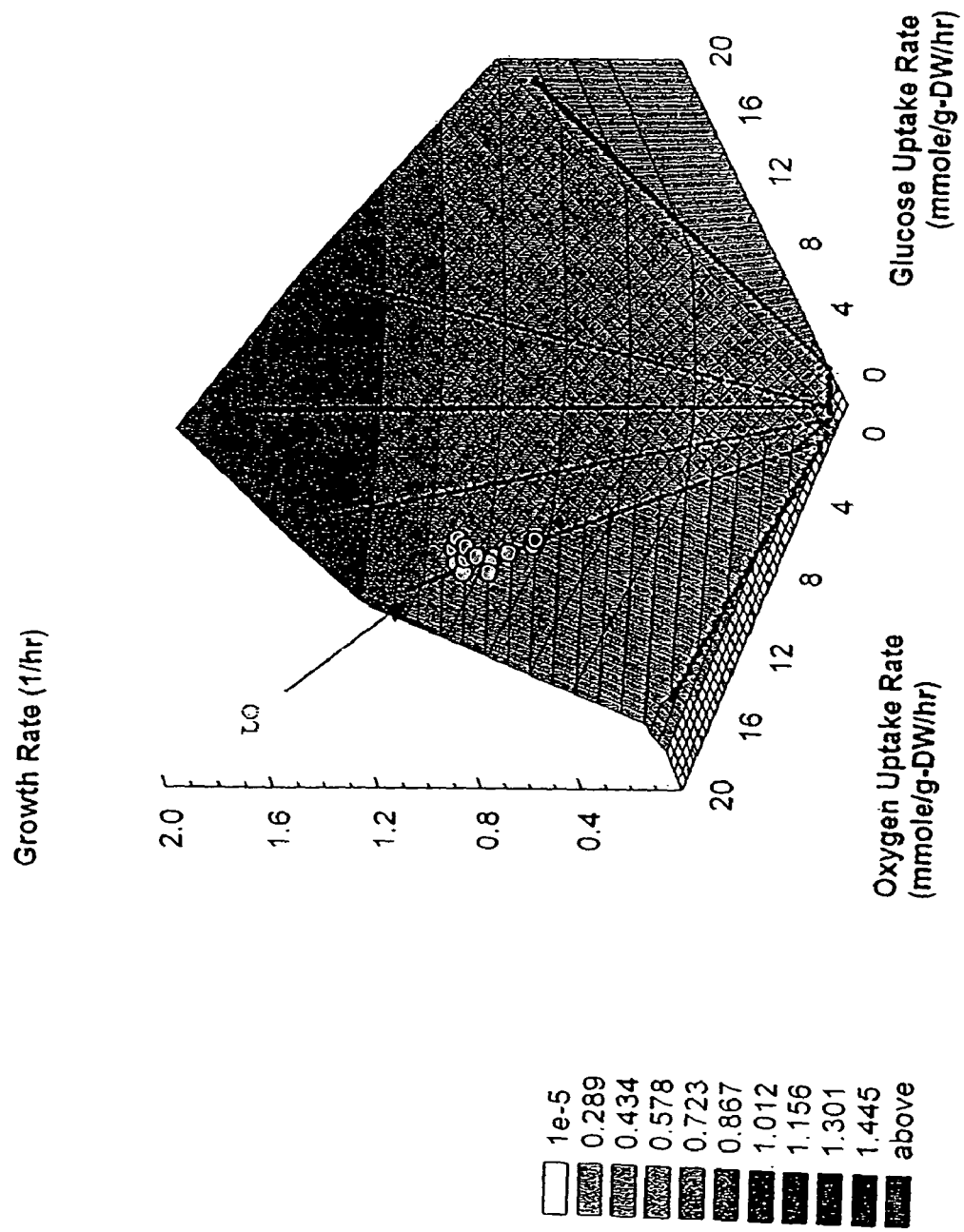
FIG. 11: Three-dimensional rendering of the post-evolutionary 3D growth surface over the glucose phenotypic phase plane. All data points cluster tightly on or near the LO.

In three dimensions, the measured growth rates lie on the surface of the solution space near the edge corresponding to the LO, but are not tightly clustered there (FIG. 9). We therefore kept the strain in sustained exponential growth (16) over a 40-day period (about 750 generations) using serial transfer under constant growth conditions to determine whether the metabolic phenotype would evolve (FIGS. 10 and 11). Fitness indeed increased, as shown by movement of the experimental points parallel to the LO, but there was no qualitative change in the phenotype.

EXAMPLE 5

Evolution of a Sub-Optimal *E. coli* Strain to Optimally

This Example demonstrates that *E. coli* can undergo significant phenotypic adaptation from a sub-optimal growth state to an optimal state determined in silico.

Glycerol: The glycerol-oxygen PhPP consists of 5 regions with features resembling those seen in the PhPPs for acetate, succinate and glucose. In particular, a region with futile cycles (phase 1) is separated from an acetate overflow region (phase 2) by the LO.

Figure 12:
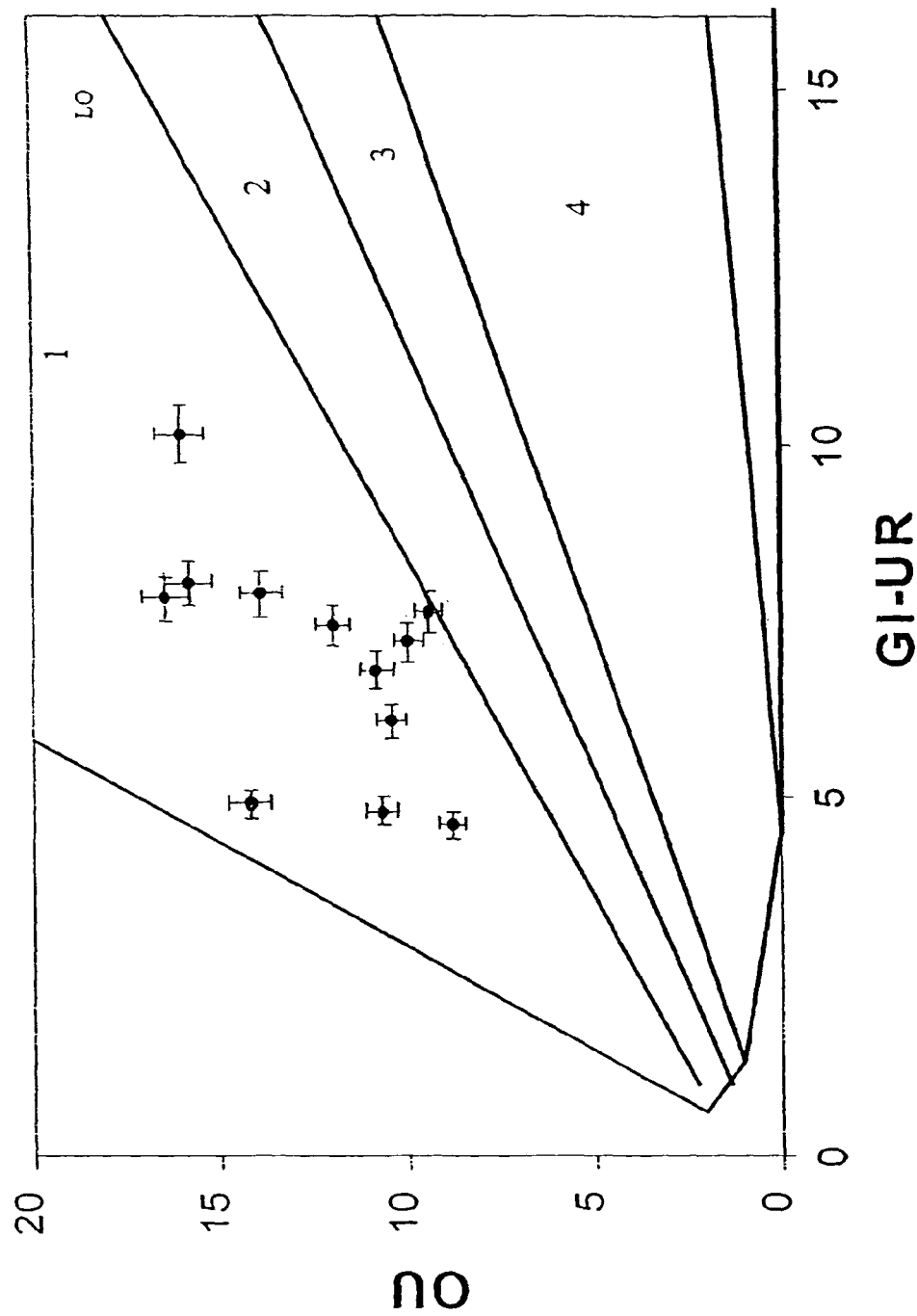
FIG. 12: Calculated and experimental values for growth on glycerol. the glycerol uptake rate, GIUR (mmole/gDW/h), and the oxygen uptake rate, OUR (mmole/gDW/h), are shown in the phenotype phase plane. The LO is shown in indicated. The experimental data points are confined to region 1, characterized by futile cycles and suboptimal growth rates.
Figure 13:
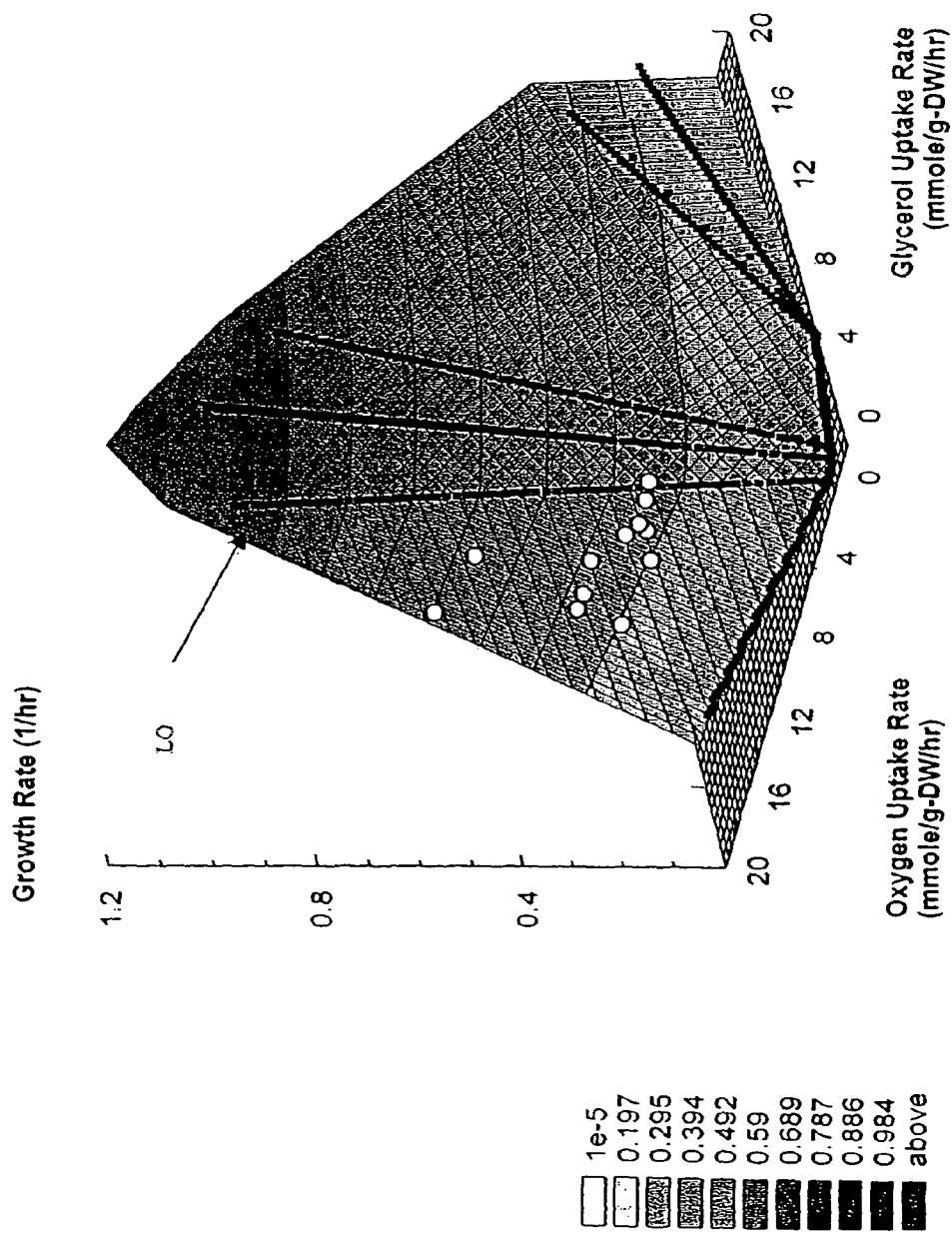
FIG. 13: Three-dimensional rendering of growth rates graphed over the glycerol phenotypic phase plane. The x and y axes represent the same variables as in FIG. 12. The z-axis represents the cellular growth rate, and the optimal growth rate indicated on the legend. No data points lie near the LO.

The growth performance over a range of glycerol concentrations was experimentally determined as before. In sharp contrast to growth on malate or glucose, however, the experimental values for growth were scattered throughout phase 1, far from the LO (FIG. 12) and the surface of optimality (FIG. 13). Unlike the other substrates examined, glycerol thus supports only sub-optimal growth of *E. coli* K-12.

As before, we therefore performed a long-term adaptive growth experiment, this time using glycerol as the sole carbon source. The original strain was again kept in prolonged exponential growth for 40 days by serial transfer (17), maintaining a temperature of 30° C., a glycerol concentration of 2 g/L, and sufficient oxygenation. Growth rate, glycerol uptake rate (GIUR) and OUR were determined every ten days.

Figure 14:
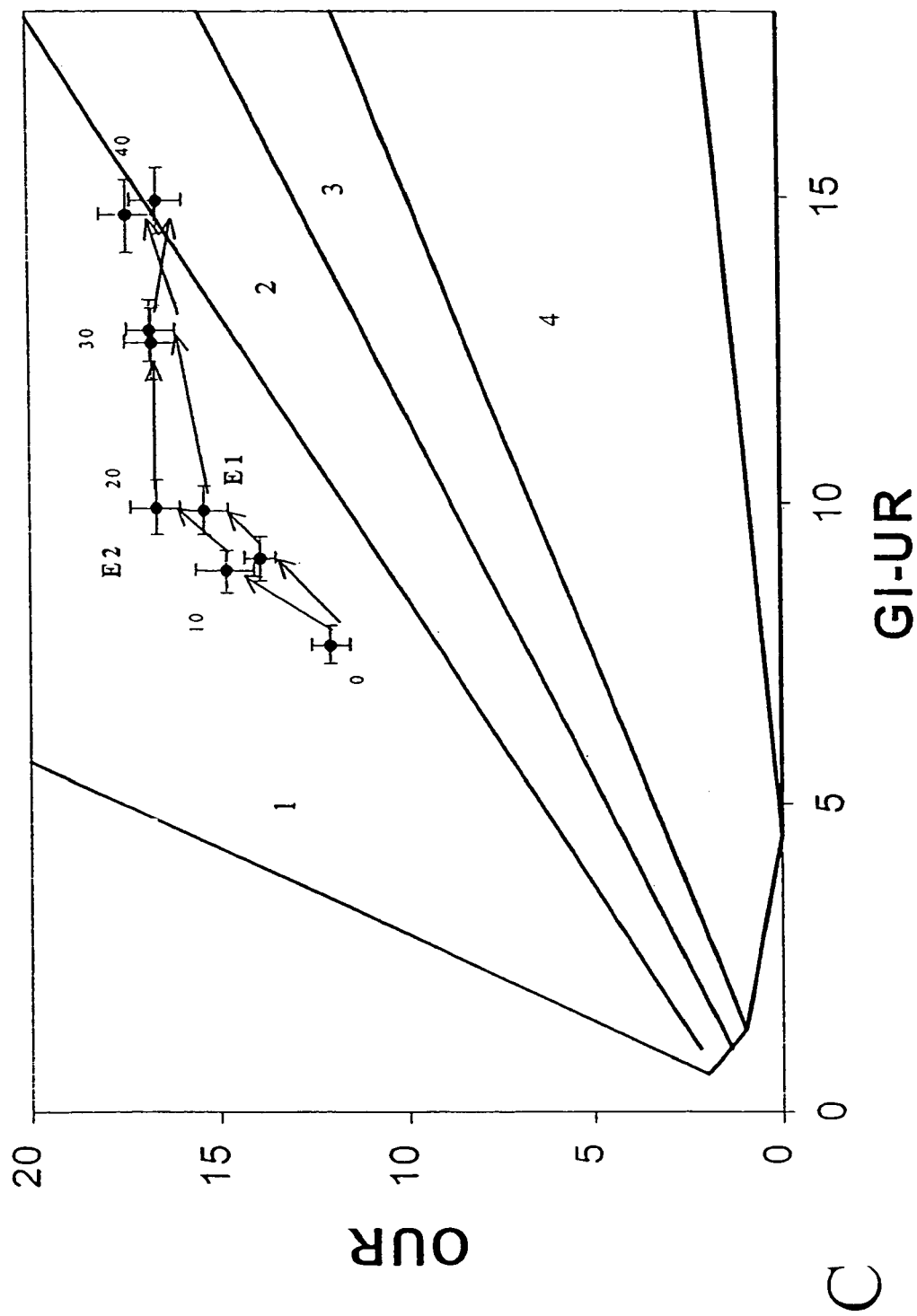
FIG. 14: The glycerol uptake rate (GIUR) plotted against the oxygen uptake rate (OUR) with experimental values for adaptive evolution experiments. The starting point of evolution is indicated (day 0). Experimental values for the first evolutionary trajectory are indicated by E1, while values for the second evolutionary trajectory are indicated by E2. In both experiments, the initial strain converges towards a similar endpoint on the LO, representing optimal growth rates.
Figure 15:
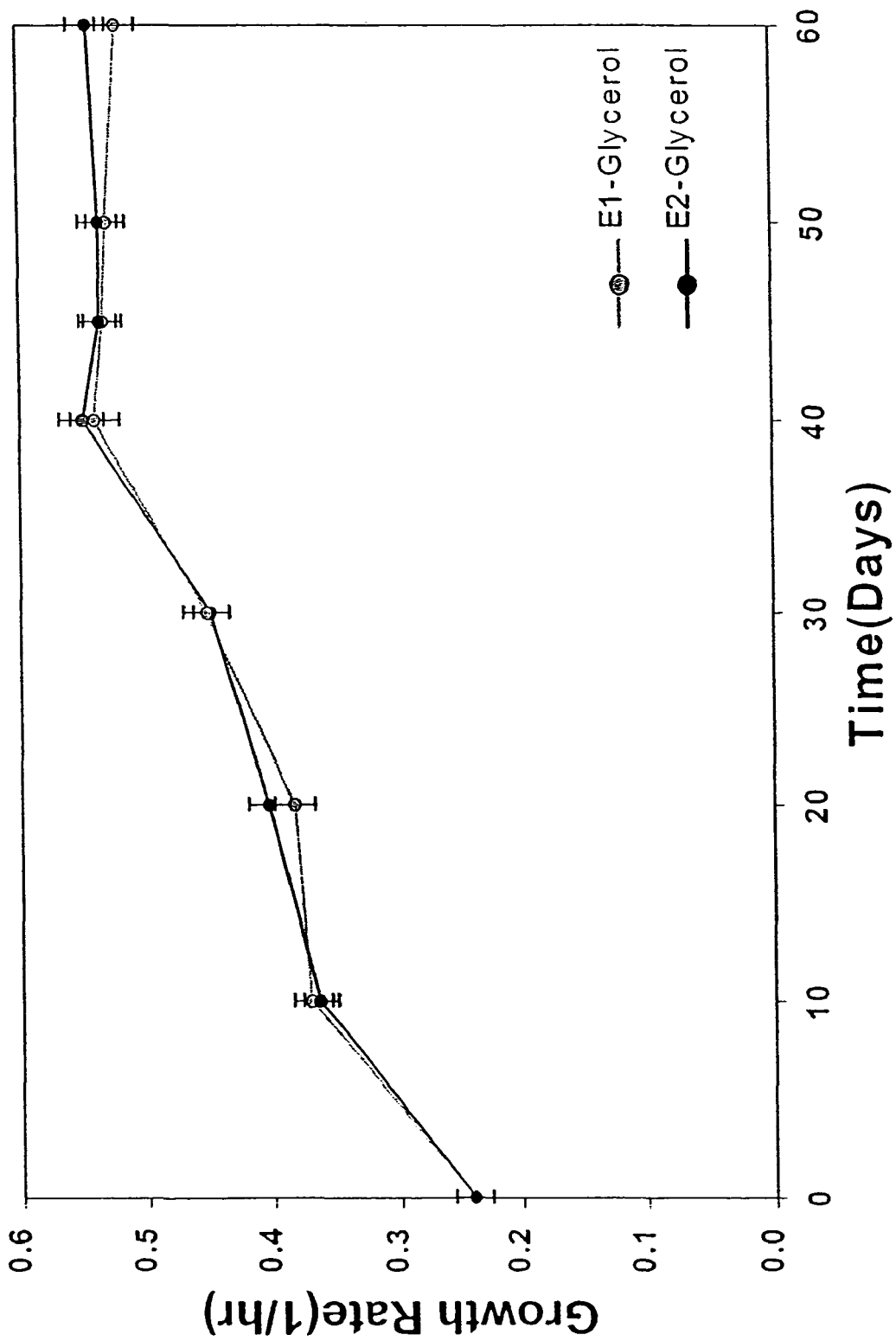
FIG. 15: Change in growth rate in units or $hr^{-1}$, with time for adaptive evolution experiments on glycerol. Both experiments reveal a similar adaptation profile, with increased fitness and a doubling of the growth rate.
Figure 16:
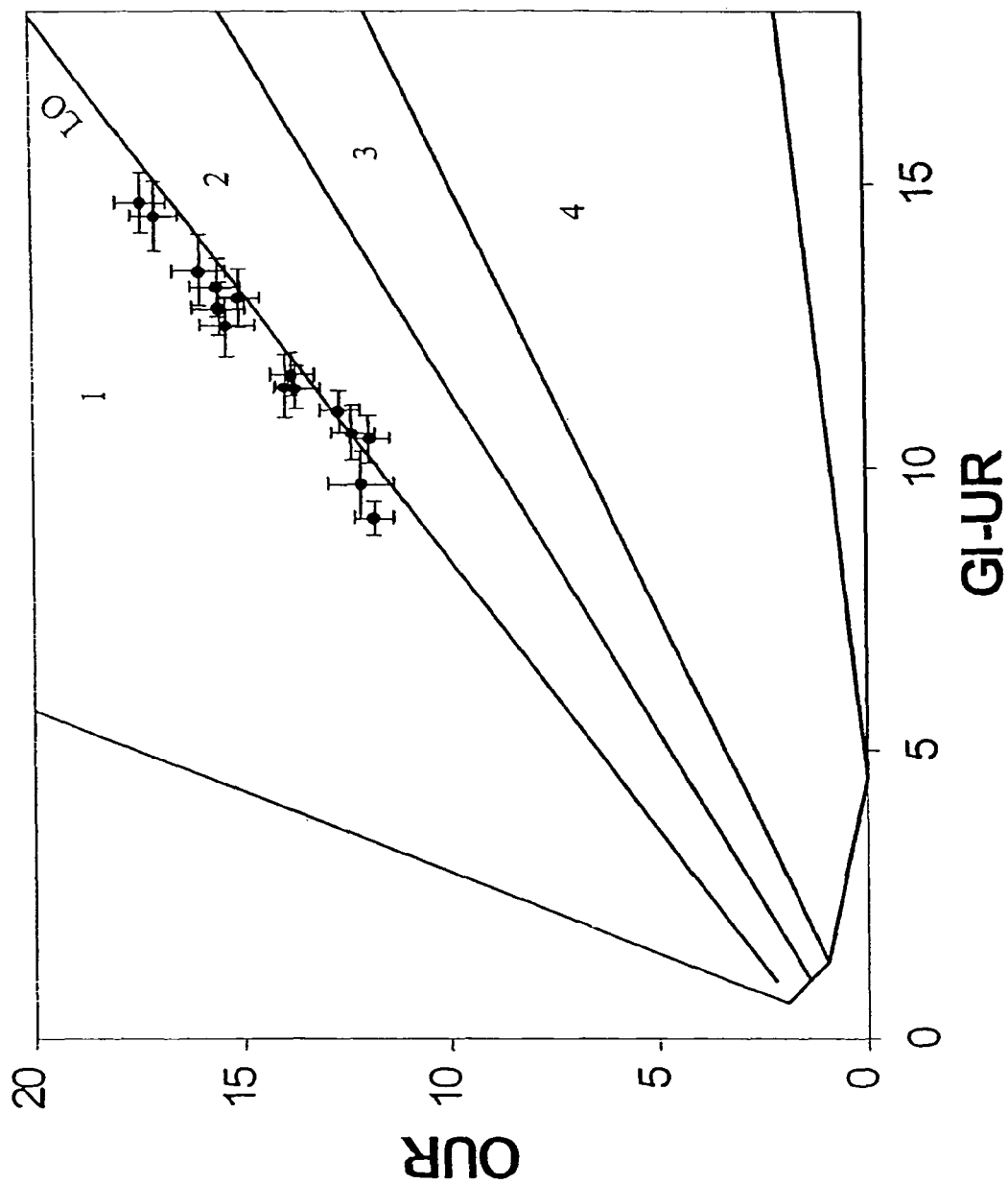
FIG. 16: The glycerol-oxygen phenotypic phase plane with experimental values for growth on glycerol after the adaptive evolution experiments. All values cluster tightly on or near the LO. Data represents the titration of the carbon source and the quantitative effect of moving along the LO.
Figure 17:
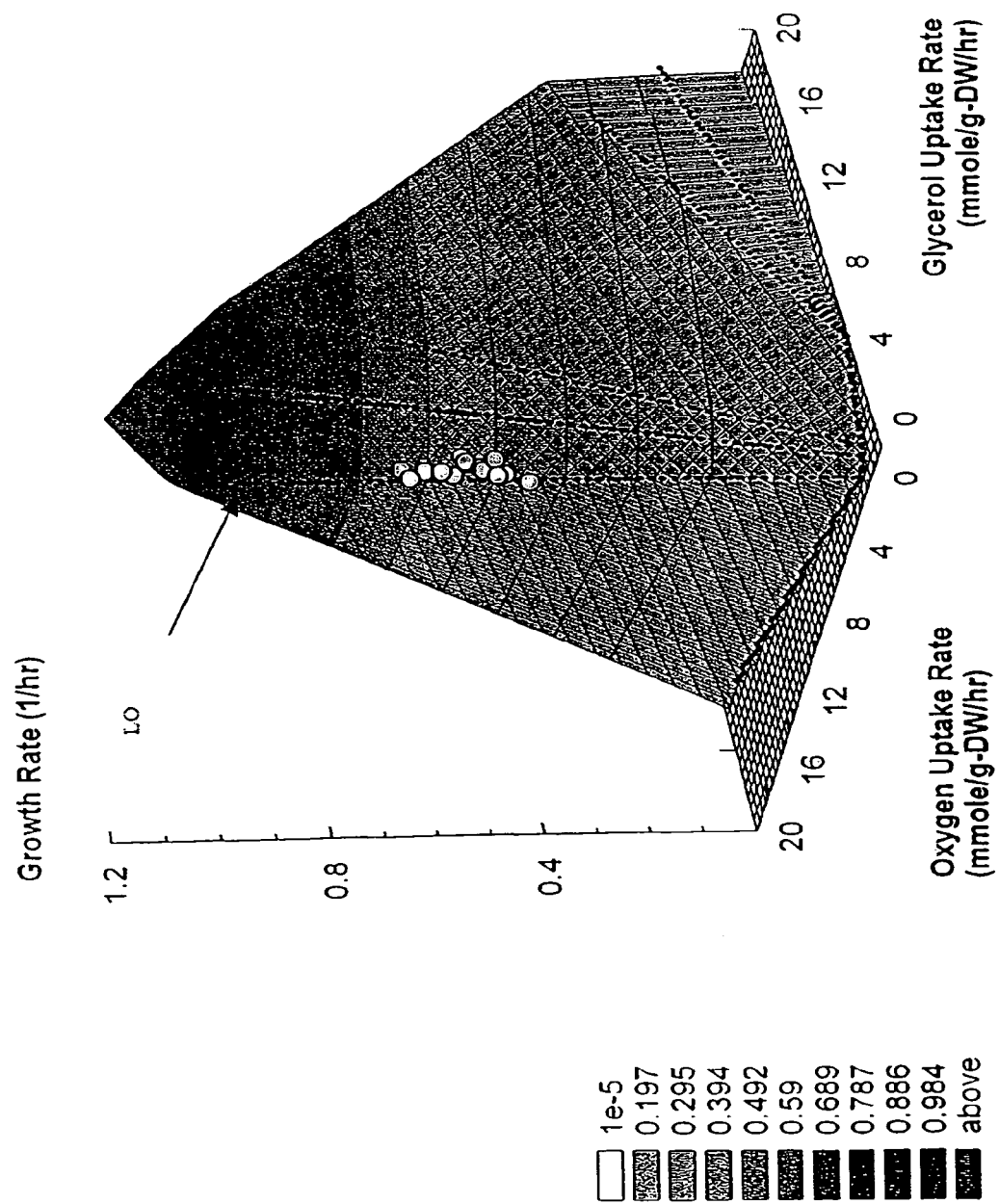
FIG. 17 Three-dimensional rendering of the post-evolutionary phase surface. All data points cluster tightly on or near the LO.

A forty-day evolutionary path (E1) was traced in phase 1, eventually converging on the LO (FIG. 14). During this period, the growth rate more than doubled from 0.23 $hr^{-1}$ to 0.55 $hr^{-1}$ (FIG. 15). Further testing of the resulting evolved strain (which was frozen and stored) revealed higher specific growth rates and biomass yields than the parental strain. All of the data obtained fell on or near the LO as it had on the final day of the long-term culture (FIGS. 16 and 17), indicating that the evolved strain had attained an optimal growth performance on glycerol consistent with predictions in silico. A second, independent adaptation experiment gave a similar but not identical evolutionary trajectory (E2), converging near the same endpoint. *E. coli* can therefore undergo significant phenotypic adaptation from a sub-optimal growth state to an optimal state determined in silico.

Optimal growth performance of bacteria thus appears to conform with the predictions of in silico analysis. On some substrates, such as acetate and succinate, the cell may display optimal growth, whereas on others such as glucose and glycerol it may not. In the latter case growth evolves towards a phase plane predicted optimal performance.

All of the references cited herein are incorporated by reference. Although the invention has been described with reference to the above examples, it will be understood that modifications and variations are encompassed within the spirit and scope of the invention. Accordingly, the invention is limited only by the following claims.

What is claimed is:

1. A method for achieving an optimal function of a biochemical reaction network in an eukaryotic cell comprising:
    (a) calculating optimal properties of a biochemical reaction network by applying a computational optimization method to a list of reactions representing said biochemical reaction network;
    (b) altering said list of reactions in the biochemical reaction network and re-computing the optimal properties;
    (c) repeating (b) until a desired optimal function is reached;
    (d) constructing an eukaryotic cell having the genetic makeup containing the biochemical reactions which result from (c);
    (e) placing the eukaryotic cell constructed under (d) in culture under a specified environment to obtain a population of eukaryotic cells; and
    (f) cultivating the eukaryotic cells as in step (e) for a sufficient period of time and under conditions to allow the cells to evolve to the desired optimal function determined under (c), wherein the biochemical reaction network comprises a comprehensive biochemical reaction network.

2. The method of claim 1, wherein the biochemical network is a metabolic network.

3. The method of claim 1, wherein the biochemical network is a regulatory network.

4. The method of claim 1, wherein the eukaryotic cells are yeast, fungal cells, animal cells or cell lines.

5. The method of claim 4, wherein the yeast cell is *S. cerevisiae*.

6. The method of claim 4, wherein the animal cells or cell lines are human.

7. The method of claim 4, wherein the animal cells or cell lines are selected from primate, rodent, amphibian or insect.

8. The method of claim 1, wherein step (d) comprises altering one or more genes in the eukaryotic cell.

9. The method of claim 8, wherein altering comprises introduction of a gene or genes into the eukaryotic cell.

10. The method of claim 8, wherein altering comprises modification of an endogenous gene or genes in the eukaryotic cell.

11. The method of claim 1, wherein the biochemical reaction network comprises a substantially whole biochemical reaction network.

* * * * *